(12) United States Patent
Fukui et al.

(10) Patent No.: US 8,753,877 B2
(45) Date of Patent: Jun. 17, 2014

(54) INCUBATOR

(75) Inventors: Shinji Fukui, Oura-gun (JP); Yasuhiko Yokoi, Ota (JP); Akifumi Iwama, Tukuba (JP); Hiroshi Yamamoto, Neyagawa (JP); Jirou Ohnishi, Ota (JP)

(73) Assignee: Panasonic Healthcare Co., Ltd., Toon-shi, Ehime (JP)

( * ) Notice: Subject to any disclaimer, the term of this patent is extended or adjusted under 35 U.S.C. 154(b) by 439 days.

(21) Appl. No.: 13/021,352

(22) Filed: Feb. 4, 2011

(65) Prior Publication Data

US 2011/0189765 A1 Aug. 4, 2011

(30) Foreign Application Priority Data

Feb. 4, 2010 (JP) ................................ 2010-023606

(51) Int. Cl.
*C12M 1/00* (2006.01)
*C12M 3/00* (2006.01)
*B01L 7/00* (2006.01)

(52) U.S. Cl.
CPC ............... *C12M 41/14* (2013.01); *C12M 23/48* (2013.01); *B01L 7/52* (2013.01)
USPC ........................................ 435/303.1; 435/243

(58) Field of Classification Search
CPC ......... C12M 41/14; C12M 23/48; B01L 7/52; B01L 7/00; B01L 2300/0829; A01K 41/00; A01K 41/02; A01K 41/04; A01K 1/0218; A01K 1/033
USPC ................. 435/303.1; 119/311, 314
See application file for complete search history.

(56) References Cited

U.S. PATENT DOCUMENTS

| | | | |
|---|---|---|---|
| 4,336,329 A * | 6/1982 | Hesse et al. ....................... 435/3 |
| 4,742,798 A * | 5/1988 | Blackett ....................... 119/218 |
| 6,225,110 B1 * | 5/2001 | Cecchi et al. ............. 435/303.1 |
| 2001/0006812 A1 | 7/2001 | Tamaoki et al. |
| 2006/0194193 A1 | 8/2006 | Tsuruta et al. |
| 2009/0098641 A1 * | 4/2009 | Grant ........................ 435/286.1 |
| 2009/0221064 A1 | 9/2009 | Osawa et al. |

FOREIGN PATENT DOCUMENTS

| | | |
|---|---|---|
| CN | 101400779 A | 4/2009 |
| EP | 2 067 849 A1 | 6/2009 |
| JP | 2006-54 A | 1/2006 |
| JP | 2009-022221 A | 2/2009 |
| JP | 2009-136232 A | 6/2009 |

OTHER PUBLICATIONS

European Office Action dated Sep. 4, 2012, issued in corresponding European Patent Application No. 11 000 818.2 (4 pages).
European Search Report dated Jun. 7, 2011, issued in corresponding European Patent Application No. 11000818.2.
European Office Action dated Jul. 10, 2013, issued in corresponding European Patent Application No. 11000818.2.
Chinese Office Action dated Aug. 19, 2013, issued in corresponding Chinese Patent Application No. 201110034259.4, w/ English translation.

* cited by examiner

*Primary Examiner* — Michael Hobbs
(74) *Attorney, Agent, or Firm* — Westerman, Hattori, Daniels & Adrian, LLP

(57) ABSTRACT

An incubator including a cultivating chamber for cultivating cultures, a water supply control unit for supplying water into the cultivating chamber through a water supply passage and adjusting the humidity of the inside of the cultivating chamber, and a filter provided in the water supply passage.

10 Claims, 16 Drawing Sheets

INCUBATOR

INCORPORATION BY REFERENCE

The present application claims priority under 35 U.S.C. §119 to Japanese Patent Application No. 2010-023606 filed on Feb. 4, 2010. The content of the application is incorporated herein by reference in its entirety.

BACKGROUND OF THE INVENTION

1. Field of the Invention

The present invention relates to an incubator having a cultivating chamber for cultivating cultures.

2. Description of the Related Art

An incubator having a cultivating chamber for cultivating cultures has been known. In this incubator, the humidity of the inside of the cultivating chamber is kept to a fixed value or more (for example, see JP-A-2009-22221). Furthermore, as one of this type of incubators, water is stocked in the cultivating chamber and the humidity of the inside of the cultivating chamber is kept to a fixed value or more by the stocked water.

With respect to the incubator in which water is stocked in the cultivating chamber and the humidity in the cultivating chamber is kept to a fixed value or more by the stocked water as described above, it is necessary to supply the cultivating chamber with water to be stocked, however, it is also required to prevent supply of water to the cultivating chamber from adversely affecting maintenance of an aseptic condition of the cultivating chamber.

SUMMARY OF THE INVENTION

The present invention has been implemented in view of the foregoing situation, and has an object to provide an incubator that can prevent water supply to a cultivating chamber from adversely affecting maintenance of an aseptic condition of the cultivating chamber.

In order to attain the above object, there is provided an incubator comprising: a cultivating chamber for cultivating cultures; a water supply control unit for supplying water into the cultivating chamber through a water supply passage and adjusting the humidity of the inside of the cultivating chamber; and a filter provided in the water supply passage.

In the above incubator, the water supply control unit may comprise an indoor decontaminating unit for supplying decontamination gas into the cultivating chamber to decontaminate the inside of the cultivating chamber, and a passage decontaminating unit for decontaminating the inside of the water supply passage by using the decontamination gas supplied to the cultivating chamber by the indoor decontaminating unit.

The above incubator may further comprise a water discharge passage for discharging water stocked in the cultivating chamber, wherein the passage decontaminating unit further decontaminates the inside of the water discharge passage by using decontamination gas supplied to the cultivating chamber by the indoor decontaminating unit.

The above incubator may further comprise a first gas passage that is connected to an upstream side of a locating position of the filter in the water supply passage at one end thereof, and also connected to the water discharge passage at the other end thereof, and a first pump that is provided on a first passage extending from a water discharge port formed at an end portion at the cultivating chamber side of the water discharge passage through the water discharge passage, the first gas passage and the water supply passage to a water supply port formed at one end portion at the cultivating chamber side of the water supply passage to suck decontamination gas from the water discharge port into the first passage and discharge the decontamination gas from the water supply port into the cultivating chamber, wherein the passage decontaminating unit drives the pump to suck the decontamination gas supplied to the cultivating chamber by the indoor decontaminating unit from the water discharge port into the first passage and discharging the decontamination gas from the water supply port into the cultivating chamber, thereby decontaminating the inside of the first passage.

The above incubator may further comprise a second gas passage that is connected to an upstream side of a locating position of the filter in the water supply passage at one end thereof and also connected to a gas discharge portion for discharging gas to the outside at the other end thereof, and a second pump that is provided on the second gas passage to suck decontamination gas from a water supply port formed at an end portion at the cultivating chamber of the water supply passage and discharge the decontamination gas through the water supply passage and the second gas passage into the gas discharge portion, whereby the passage decontaminating unit drives the second pump to suck the decontamination gas supplied to the cultivating chamber by the indoor decontaminating unit from the water supply port and discharging the decontamination gas through the water supply passage and the second gas passage into the gas discharge portion, thereby decontaminating the water supply passage.

The above incubator may further comprise: a decontamination liquid tank for stocking decontamination tank; a decontamination liquid supply passage that is connected to an upstream side of a locating position of the filter in the water supply passage and also connected to the decontamination liquid tank at the other end thereof; a third pump that is provided on the decontamination liquid passage to make the decontamination liquid flow from the decontamination liquid tank through the decontamination liquid supply passage and the water supply passage to a water supply port formed at an end portion at the cultivating chamber side of the water supply passage; and a passage decontaminating unit that drives the third pump to make the decontamination liquid flow from the decontamination liquid tank through the decontamination liquid supply passage and the water supply passage to the water supply port, thereby decontaminating the water supply passage.

According to the present invention, water can be easily supplied into the cultivating chamber under the state that the aseptic condition of the cultivating chamber can be maintained.

DETAILED DESCRIPTION OF PREFERRED EMBODIMENTS

Preferred embodiments according to the present invention will be described hereunder with reference to the accompanying drawings.

First Embodiment

Figure 1:
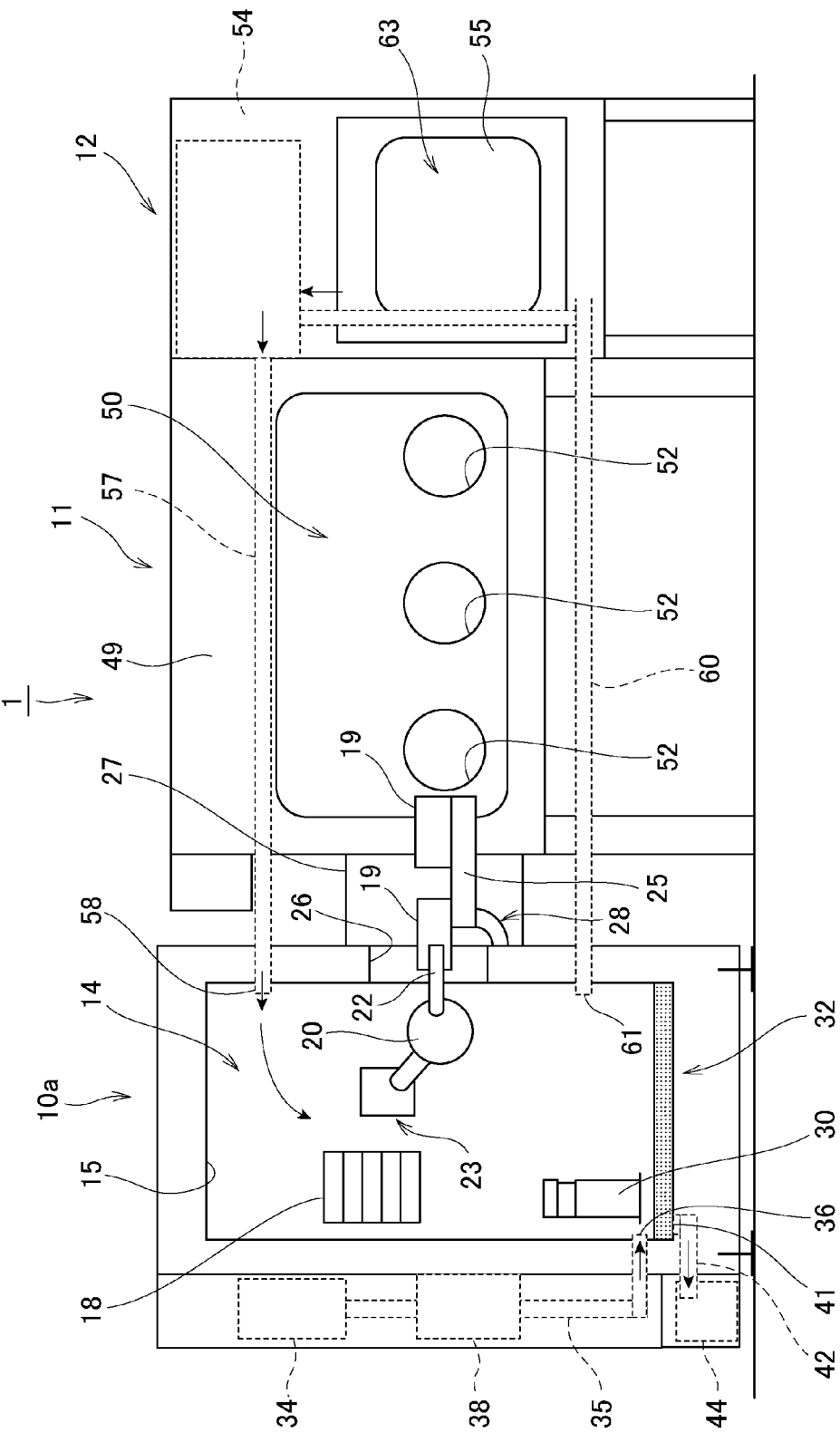
FIG. 1 is a diagram showing an incubator system according to a first embodiment.

FIG. 1 is a diagram showing an incubator system 1 according to a first embodiment.

As shown in FIG. 1, the incubator system 1 has an incubator 10a, an isolator 11 and a decontaminating unit 12.

In this specification, "decontamination" means a treatment, means or an action to prevent contamination of microorganisms or sterilize or remove microorganisms so that the state is set (made to approach) to an aseptic condition. It generally contains "sterile filtration", "sterilization", "antisepsis", etc.

Figure 2:
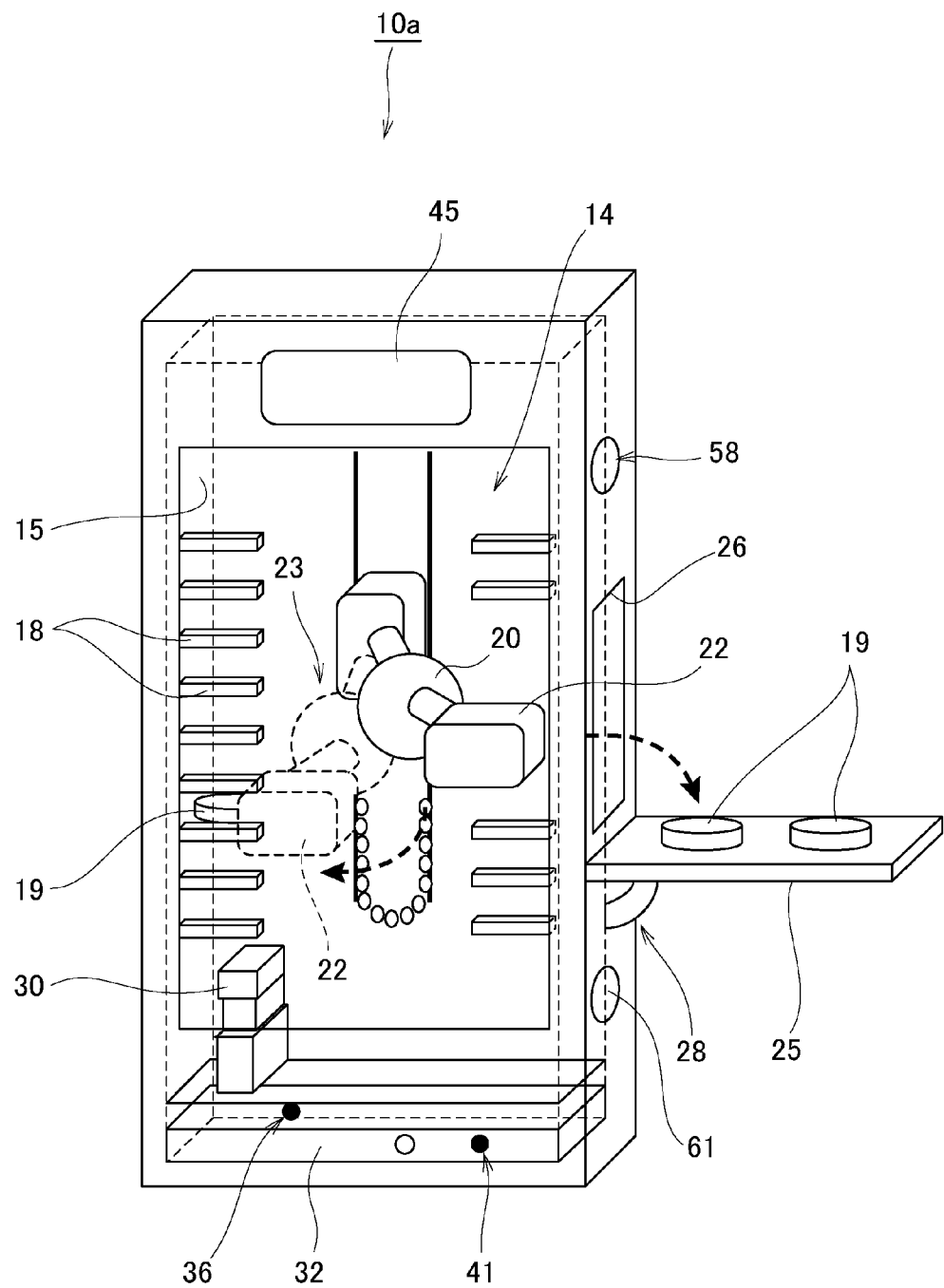
FIG. 2 is a front perspective view showing an incubator.
Figure 3:
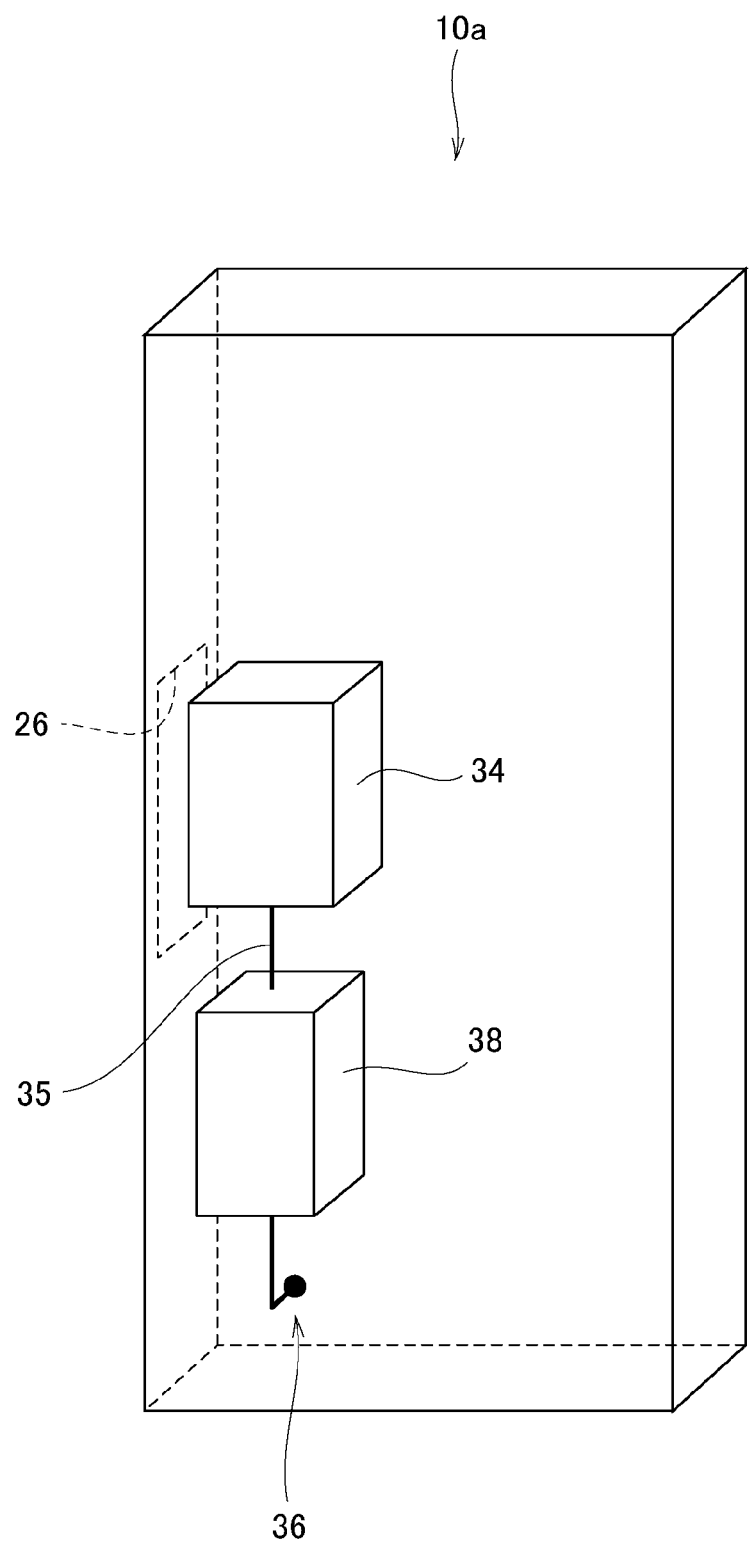
FIG. 3 is a diagram showing a back perspective view showing the incubator.

FIG. 2 is a front perspective view showing the incubator 10a, and FIG. 3 is a back perspective view showing the incubator 10a.

As shown in FIGS. 1 and 2, the incubator 10a has a cultivating chamber 14 for cultivating cultures, and keeps the temperature, the concentration of gas such as carbon dioxide, etc. and the humidity in the cultivating chamber 14 in fixed ranges so that cultures such as cells, microorganisms or the like accommodated in the cultivating chamber 14 are cultivated.

The cultivating chamber 14 has a heat-insulating (adiabatic) box body 15 constructed by providing a stainless inner box in a metal outer box. An opening is formed in the front surface of the heat-insulating box body 15, and an main door (not shown) is provided at the opening so as to be freely openable/closable through a link portion such as a hinge or the like with respect to the heat-insulating box body 15.

A locking device 16 (FIG. 6) is provided to the main door. The locking device 16 automatically locks the main door under the control of a controller 17 described later when it is necessary to lock the main door.

As shown in FIG. 2, container shelves 18 are provided in the cultivating chamber 14 so as to be located at intervals in the vertical direction, and containers 19 in which cultures are mounted are mounted on the container shelves 18.

An automatic feeder 20 is provided in the cultivating chamber 14. The automatic feeder 20 automatically feeds the containers 19 mounted on the container shelves 18 to an isolator 11 on the basis of an user's instruction. More specifically, the automatic feeder 20 has a grip portion 22 which can grip a container 19, and a feeding mechanism 23 for moving the grip portion 22. When it is instructed to feed a predetermined container 19 mounted on a predetermined container shelf 18, the automatic feeder 20 moves the grip portion 22 to the locating position of the grip portion 22 by the feeding mechanism 23. The grip portion 22 grips the container 19 concerned, and feeds the container 19 onto a movable table 25 while keeping the state that the container 19 is gripped by the grip portion 22 and mounts the container 19 concerned on the movable table 25.

Here, a feeding opening 26 through which a container to be fed to the isolator 11 is passed is formed in a side wall of the cultivating chamber 14 at the isolator 11 side, and a connection portion 27 intercommunicating with the feeding opening 26 is provided so that the incubator 10a and the isolator 11 are connected to each other through the connection portion 27 under the state that flow-in of air from the outside is interrupted.

A door mechanism (not shown) for closing the opening. When the incubator 10a and the isolator 11 are not connected to each other under the state that a container 19 is movable between the incubator 10a and the isolator 11, the feeding opening 26 is closed by the door. On the other hand, when the incubator 10a and the isolator 11 are connected to each other under the state that a container 19 is movable between the incubator 10 and the isolator 11, the door is opened to open the feeding opening 26, and the cultivating chamber 14 of the incubator 10a and the inside of the isolator 11 intercommunicate with each other. Furthermore, as described above, the movable table 25 serves as a space in which a container 19 to be fed from the cultivating chamber 14 to the isolator 11 by the automatic feeder 20 is mounted.

When a container 19 is moved between the incubator 10a and the isolator 11, the container is fed to the feeding opening 26 by the feeding mechanism 23, and fed through the opening portion opened by the door mechanism to the outside of the incubator 10a. At the same time, the movable table 25 is moved to the neighborhood of the feeding opening 26 by a movable table mechanism (not shown), and the container 19 is mounted onto the movable table 25 by the feeding mechanism 23 and then fed into a working chamber by the movable table mechanism.

The cultivating chamber 14 is provided with an observing device 30 for observing cultures. The observing device 30 has a function of picking up images of a culture accommodated in a container 19 when the container 19 is mounted at a predetermined position (not shown) in the observing device 3.

More specifically, the observing device 30 has an imaging device for picking up an image of the whole of the accommodating portion of the culture in the container 19 to pick up an image of the whole of the culture, an imaging device for picking up an image obtained by microscopically observing the culture accommodated in the container 19, etc. The image of the culture are picked up by these imaging devices, whereby the culture is observed. A signal representing the image picked up by these imaging devices is subjected to A/D conversion and then output to a controller 17 described later, and the signal is arbitrarily saved as data under the control of the controller 17.

A container for which observation is required is fed to a predetermined position in the observing device 30, whereby cultures in all the containers 19 accommodated in the incubator 10a can be performed without damaging the internal environment of the cultivating chamber.

Furthermore, the cultivating chamber 14 is provided with a humidifying water stock unit 32 in which water used to keep the humidity of the cultivating chamber 14 to a predetermined value (for example, 90%) or more (hereinafter referred to as "humidifying water") is stocked. The humidifying water stock unit 32 is a box-shaped tray having an opened top surface, and provided so as to expand substantially over the whole area of the bottom surface of the cultivating chamber 14. A shown in FIG. 3, a water supply tank 34 in which humidifying water to be supplied to the humidifying water stock unit 32 is stocked is provided to the back surface of the incubator 10a. One end of a water supply pipe 35 (water supply passage) is connected to the water supply tank 34, and the other end of the water supply pipe 35 is connected to a water supply port 36 formed in the incubator 10a. The humidifying water stocked in the water supply tank 34 is supplied to the humidifying water stock unit 32 through the water supply pipe 35 and the water supply port 36.

As shown in FIGS. 1 and 3, a water supply unit 38 for executing a predetermined treatment described later to the humidifying water supplied from the water supply tank 34 to the humidifying water stock unit 32 is provided at the downstream side of the water supply tank 34 along the water supply pipe 35. In this embodiment, the humidifying water stock unit 32 is provided with a water level sensor 40 (FIG. 6) for detecting the water level of humidifying water stocked in the humidifying water stock unit 32, and humidifying water is arbitrarily supplied from the water supply tank 34 to the humidifying water stock unit 32 in accordance with a detection value of the water level sensor 40, whereby the water level of the humidifying water in the humidifying water stock unit 32 is kept in a predetermined range and the humidity of the cultivating chamber 14 is kept to a predetermined value or more.

Furthermore, a water discharging port 41 is formed in the humidifying water stock unit 32 to discharge humidifying water stocked in the humidifying water stock unit 32 to the outside of the incubator 10a. One end of a water discharging pipe 42 (water discharging passage) is connected to the water discharging port 41, and an automatic water discharger 44 (FIG. 1) for discharging humidifying water through the water discharging pipe 42 to the outside is connected to the other end of the water discharging pipe 42.

As shown in FIG. 2, an operation panel 45 is provided to the upper portion of the front surface of the incubator 10a. The operation panel 45 has a display panel 46 (FIG. 6) for displaying various kinds of information such as an operation mode, the present temperature, humidity, gas concentration of predetermined gas, etc. in the cultivating chamber 14, etc, and an operation switch 47 (FIG. 6) to be operated by a user.

As shown in FIG. 1, the isolator 11 is provided so as to be adjacent to the incubator 10a.

The isolator 11 has a working space 50 under an aseptic environment therein, and is used to perform a work for which an aseptic environment is required, for example, a work for treating materials derived from living organism such as cell regulation or the like.

Accordingly, with respect to the cultures cultivated in the cultivating chamber 14 of the incubator 10a, the user can directly access cultures and execute various kinds of tests, etc. on the cultures in the isolator 11 while the cultures are kept under the aseptic condition.

The isolator 11 will be briefly described. The isolator 11 contains a working space 50 in which the aseptic condition can be kept and into which cultures are fed from the incubator 10a every container 19. A transparent window is formed in the front wall 49 forming the front surface of the working space 50, and the inside of the working space 50 can be visually recognized through this window.

Three hand inserting portions 52 through which the hand of the user can be inserted are arranged side by side in the front surface wall 49. A globe (not shown) is joined to each hand inserting portion 52 so as to project to the working space 50. The user can insert his/her hand into any hand inserting portion 52, and executes various kinds of works on cultures with seeing the working space 50 through the window of the front wall 49 while the hand is fit in the globe.

The cultivating chamber 14 of the incubator 10a and the working space 50 of the isolator 11 are kept under the same aseptic condition, however, they are different from each other in temperature and humidity environment. The working space 50 is not subjected to special temperature and humidity management, however, the cultivating chamber 14 is managed under a condition that the temperature is set to 37° and the humidity is set to 90% RH or more in addition to the aseptic environment.

Furthermore, it is preferable for cultures under culture that the temperature and humidity variation is small, and the opening/closing operation of the door for closing the feeding opening 26 is suppressed to the requisite minimum. Therefore, the mechanism for feeding the containers 19 is constructed by two mechanisms which are disposed so as to sandwich the feeding opening 26 therebetween, and the door concerned is opened/closed only when a container 19 is delivered between the two mechanisms.

Furthermore, as shown in FIG. 1, a decontaminating unit 12 is provided so as to be adjacent to the isolator 11.

The decontaminating unit 12 has a decontamination gas generating/removing unit 54 and a pass box 55 provided at the lower side of the decontamination gas generating/removing unit 54.

The decontamination gas generating/removing unit 54 has at least two functions of a decontamination gas generating function of generating decontamination gas by ultrasonically atomizing hydrogen peroxide solution as decontamination agent solution for decontaminating the inside of the cultivating chamber 14 of the incubator 10a, and a decontamination gas removing function of subjecting a predetermined treatment to gas containing decontamination gas to remove the decontamination gas.

One end of a decontamination gas supply pipe 57 is connected to the decontamination gas generating/removing unit 54, and the other end of the decontamination gas supply pipe 57 is connected to a decontamination gas supply port 58 formed in the cultivating chamber 14 of the incubator 10a. The decontamination gas occurring in the decontamination gas generating/removing unit 54 is supplied through the decontamination gas supply pipe 57 and the decontamination gas supply port 58 into the cultivating chamber 14 when the operation mode is a decontamination mode (described later). The decontamination gas supplied into the cultivating chamber 14 is irradiated with ultraviolet rays by an ultraviolet lamp (not shown) provided in the cultivating chamber 14 to be decomposed into water and oxygen after the decontamination of the cultivating chamber 14 is finished, thereby rendering the decontamination gas harmless.

Furthermore, one end of a decontamination gas discharging pipe 60 is connected to the decontamination gas generating/removing unit 54, and the other end of the decontamination gas discharging pipe 60 is connected to a decontamination gas discharging port 61 formed in the cultivating chamber 14 of the incubator 10a. In order to decontaminate the inside of the cultivating chamber 14, decontamination gas supplied into the cultivating chamber 14 is returned through the decontamination gas discharging port 61 and the decontamination gas discharging pipe 60 to the decontamination gas generating/removing unit 54, and removed in the decontamination gas generating/removing unit 54.

Furthermore, when a member such as a tool for working or the like is fed into the working space 50 of the isolator 11, the pass box 55 is used to decontaminate the member concerned. More specifically, when the member is fed into the working space 50 of the isolator 11, a door provided to the pass box 55 is first set to an open state, the member concerned is accommodated in a member accommodating portion 63 formed in the pass box 55, and then the door is set to a close state. When the door of the pass box 55 is set to the close state, flow-in of air from the outside of the pass box 55 into the member accommodating portion 63 is perfectly interrupted.

Subsequently, decontamination gas is filled in the member accommodating portion 63 in the pass box 55 by a mechanism (not shown) to thereby decontaminate the member in the member accommodating portion 63, and then the decontamination gas filled in the member accommodating portion 63 is removed by a mechanism (not shown).

Subsequently, the user inserts the hand inserting portion 52 and puts on the globe, opens the dedicated door interposed between the working space 50 of the isolator 11 and the member accommodating portion 63 of the pass box 55 through the globe to access the member accommodating portion 63, takes out the member form the member accommodating portion 63 and then feeds the member concerned into the working space 50. Accordingly, a desired tool can be fed into the working space 50 with keeping the aseptic condition in the working space 50 of the isolator 11.

In addition to the above mechanisms, devices, etc., the incubator 10a has a temperature adjusting device for keeping the temperature of the cultivating chamber 14 within a predetermined range, a gas concentration adjusting device for supplying predetermined gas such as carbon dioxide, oxygen or the like into the cultivating chamber 14 to adjust the gas concentration of the predetermined gas in the cultivating chamber 14, a fan for circulating air in the cultivating chamber 14, various kinds of sensors for detecting the temperature of the cultivating chamber 14, the gas concentration of the predetermined gas, the humidity, etc., and various kinds of mechanisms and devices required to cultivate cultures, such as an ultraviolet lamp for irradiating decontamination gas supplied to the cultivating chamber 14 with ultraviolet rays to decompose the decontamination gas into water and oxygen and render the decontamination gas harmless, etc. In order to clarify the description, these mechanisms and devices are omitted from the illustrations of FIGS. 1 to 3.

Figure 4:
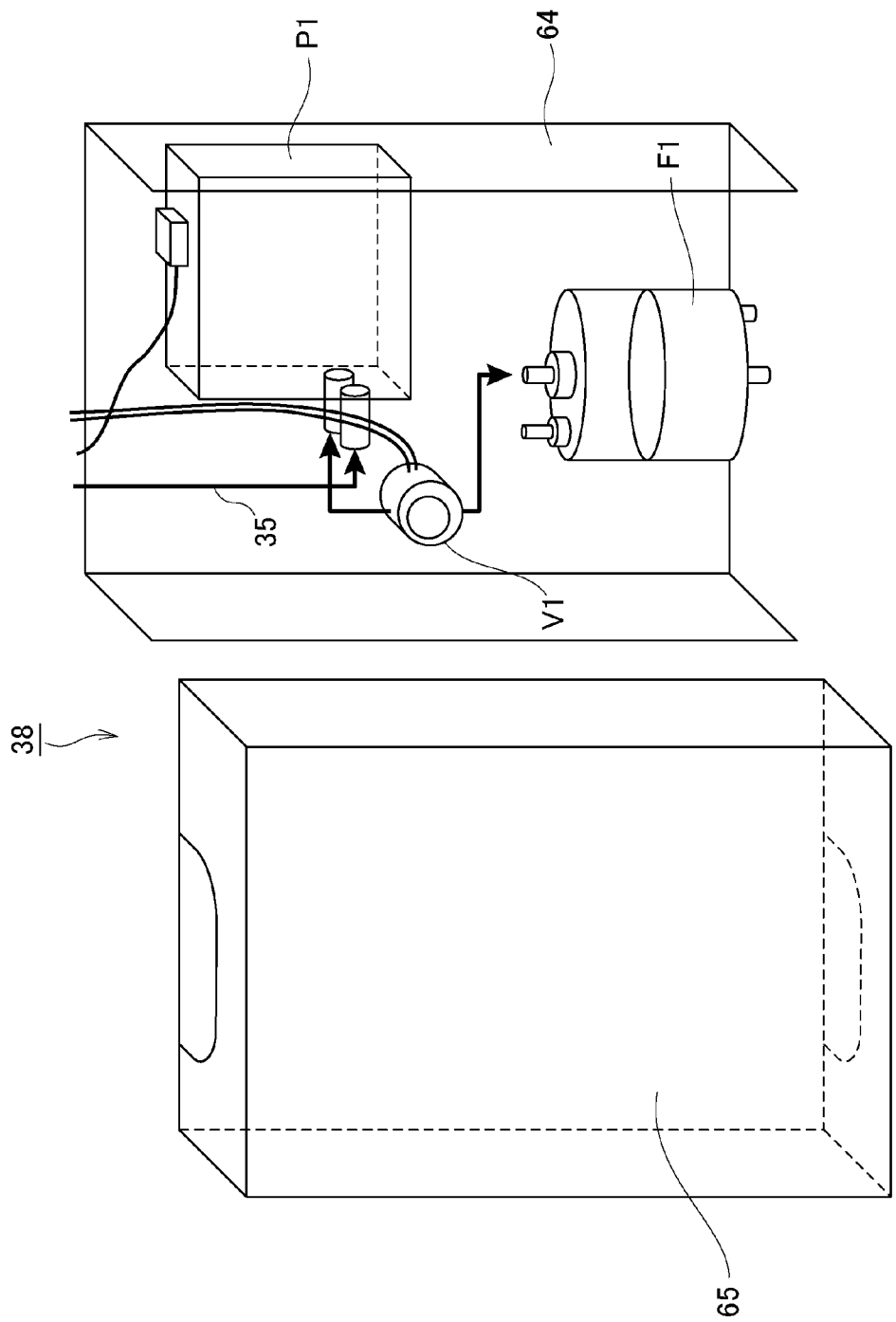
FIG. 4 is an exploded perspective view of a water supply unit.

FIG. 4 is an exploded perspective view showing the water supply unit 38.

As shown in FIG. 4, the water supply unit 38 is formed by bending both the right and left ends of a plate-shaped member, and it has a unit base portion 64 to which various kinds of equipment are secured, and a box-shaped unit lid portion 65 covering the unit base portion 64. The unit lid portion 65 is secured to the unit base portion 64 under the state that the unit base portion 64 is covered by the unit lid portion 65, whereby the outer shape of the water supply unit 38 is formed.

As shown in FIG. 4, the water supply pipe 35 connected to the water supply tank 34 is connected to a supply side pump P1. The supply-side pump P1 is a pump for supplying humidifying water stocked in the water supply tank 34 to the humidifying water stock unit 32, and the humidifying water is supplied from the water supply tank 34 to the humidifying water stocking unit 32 in accordance with the driving of the supply-side pump P1. A filter F1 described later is provided on the water supply pipe 35, and thus the supply-side pump P1 is provided to apply pressure which is required to enable the humidifying water to surely pass through the filter F1 at a predetermined flow rate. [0027]

A supply-side electromagnetic valve V1 is provided at the downstream side of the supply-side pump P1 along the water supply pipe 35 in the water supply unit 38. The supply-side electromagnetic valve V1 is a valve for permitting or stopping passage of humidifying water flowing from the water supply tank 34 to the humidifying water stock unit 32. When the valve is under an open state, supply of humidifying water from the water supply tank 34 to the humidifying water stock unit 32 is enabled, and when the valve is under a close state, the supply of humidifying water from the water supply tank 34 to the humidifying water stock unit 32 is stopped.

The filter F1 is provided at the downstream side of the supply-side electromagnetic valve V1 along the water supply pipe 35.

The filter F1 is a filter for sterilizing humidifying water passing through the filter F1, and it comprises a filter which filtrates fluid such as gas or liquid to exclude fine particles existing before the filtration and approach the fluid to a dust-free and aseptic state without limit (for example, hepafilter, millipack produced by Millipore company or the like). That is, the filter F1 sterilizes passing humidifying water, and also sterilizes passing gas.

As described above, according to this embodiment, the filter F1 for sterilizing humidifying water is provided on the water supply pipe 35. Accordingly, when humidifying water is supplied to the humidifying water stock unit 32, humidifying water containing fungus, etc. is prevented from being supplied to the humidifying water stock unit 32. Accordingly, there can be surely prevented occurrence of such a situation that the aseptic condition of the cultivating chamber 14 is adversely affected. Furthermore, the filter F1 provided on the water supply pipe 35 has a function of sterilizing gas passing therethrough. Therefore, gas containing fungus or the like can be surely prevented from flowing from the upstream side of the filter F1 into the cultivating chamber 14 through the water supply pipe 35 while no humidifying water is supplied, and thus the aseptic condition of the cultivating chamber 14 can be expected to be perfectly kept.

The water supply port 36 is connected to the filter F1 through the water supply pipe 35, and humidifying water passing through the filter F1 is supplied through the water supply port 36 into the humidifying water stock unit 32.

Figure 5:
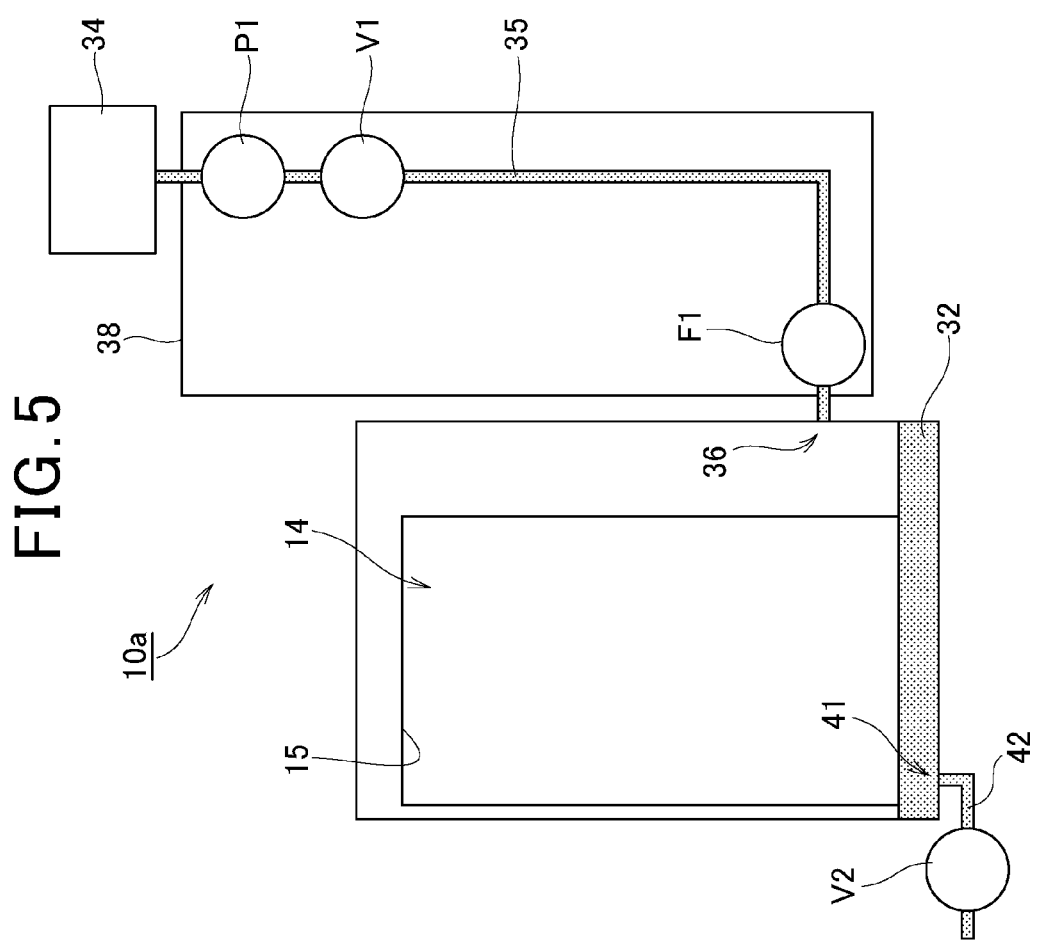
FIG. 5 is a diagram showing the construction of the incubator.

FIG. 5 is a diagram showing the incubator 10a.

As shown in FIG. 5, one end of the water supply pipe 35 is connected to the water supply tank 34, and the other end of the water supply pipe 35 is connected to the water supply port 36 formed in the cultivating chamber 14 of the incubator 10a. As described above, the supply-side pump P1, the supply-side electromagnetic valve V1 and the filter F1 are successively provided from the upstream side to the downstream side in this order in the water supply pipe 35.

Furthermore, the water discharging port 41 for discharging humidifying water stocked in the humidifying water stock unit 32 is formed in the humidifying water stock unit 32, and one end of the water discharging pipe 32 is connected to the water discharging port 41. A water discharging pipe 42 is provided with a discharge-side electromagnetic valve V2 for permitting or stopping flow of humidifying water of the water discharging pipe 42. When the discharge-side electromagnetic valve V1 is set to an open state, humidifying water stocked in the humidifying water stock unit 32 is discharged through the water discharging pipe 42. When the discharge-side electromagnetic valve V2 is set to a close state, the discharge of humidifying water stocked in the humidifying water stock unit 32 is stopped.

Figure 6:
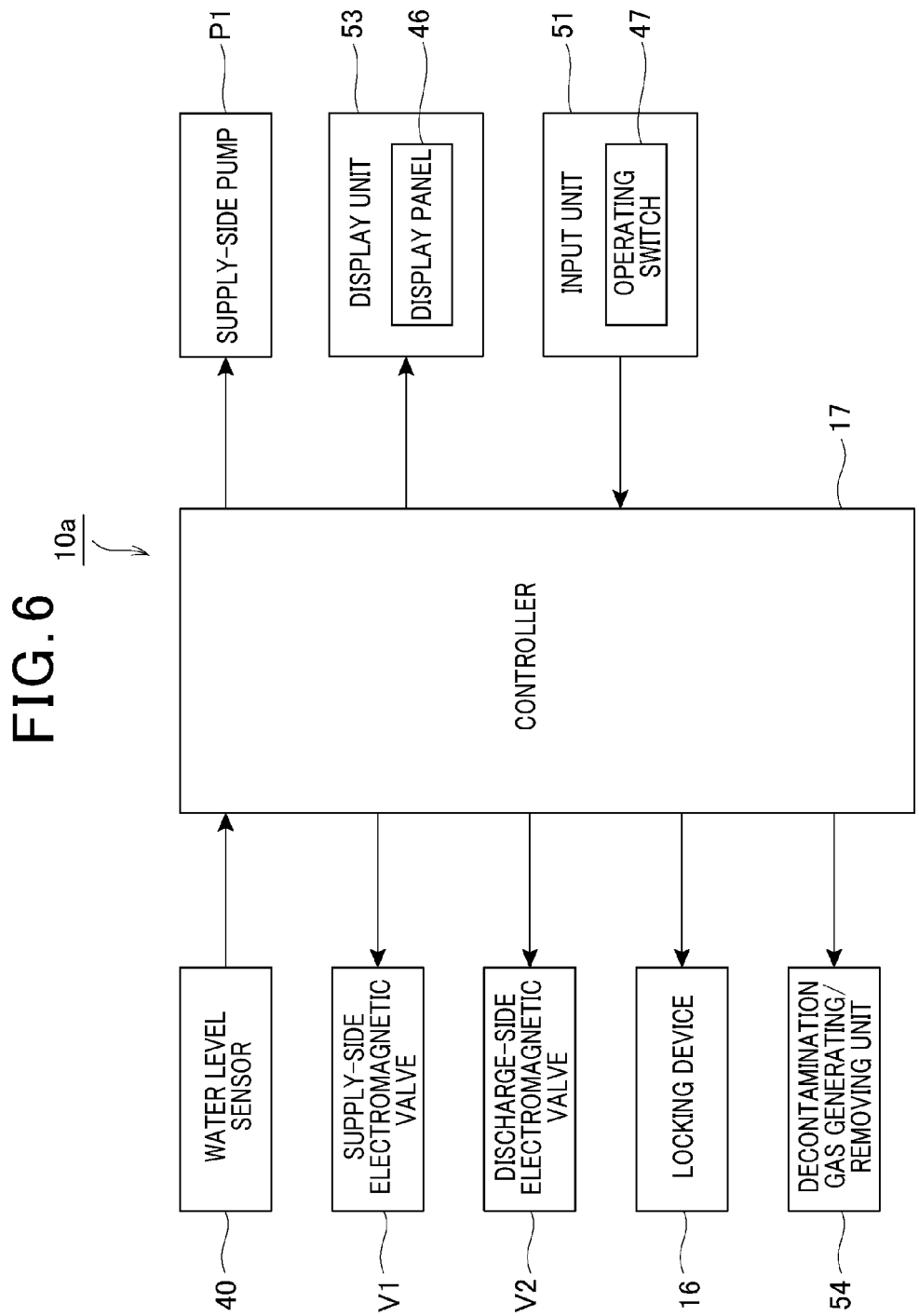
FIG. 6 is a diagram showing a functional construction of the incubator.

FIG. 6 is a block diagram showing the functional construction of an incubator 10a, and particularly is a block diagram showing a main part necessary to describe the present invention.

The controller 17 centrically controls each part of the incubator 10a, and has CPU as an operation executing unit, ROM as a storage unit, RAM functioning as a work area of CPU and other peripheral circuits.

The water level sensor 40 is a sensor for detecting whether the actual water level of humidifying water stocked in the humidifying water stock unit 32 is higher than a predetermined water level. The controller 17 determines whether the water level of the humidifying water stocked in the humidifying water stock unit 32 is higher than the predetermined water level or not.

The display unit 53 has a display panel 46, and displays various kinds of information on the display panel 46 under the control of the controller 17.

The input unit 51 is connected to the operating switch 47, detects a user's operation executed on the operating switch 47 and outputs an operation signal representing the operation concerned to the controller 17.

The controller 17 is connected to the supply-side electromagnetic valve V1 and the discharge-side electromagnetic valve V2, and controls the opening/closing state of these electromagnetic valves V1 and V2.

Furthermore, the controller 17 is connected to the supply-side pump P1, and controls the operation of the supply-side pump P1.

Still furthermore, the controller 17 controls the locking device 16, and arbitrarily locks the main door for opening/closing the front opening of the cultivating chamber 14.

Still furthermore, the controller 17 controls the decontamination gas generating/removing unit 54, and atomizes hydrogen peroxide solution (or water) by using ultrasonic waves in the decontamination gas generating/removing unit 54 to generate decontamination gas.

The incubator 10a according to this embodiment has a decontamination mode as an operation mode. The decontamination mode is an operation mode for performing decontamination in the cultivating chamber 14 by using decontamination gas. For example, this decontamination mode is executed after cultivation of predetermined cultures is finished, and the decontamination in the cultivating chamber 14 is executed. Accordingly, when different cultures are newly cultivated in the cultivating chamber 14, cultivation of the present cultures can be prevented from being adversely affected by the cultivation of the previous cultures.

In the decontamination mode, discharge of humidifying water stocked in the humidifying water stock unit 32 and supply of new humidifying water are executed in combination with the decontamination of the cultivating chamber 14. According to this embodiment, by executing the following operation, the discharge of humidifying water and the supply of new humidifying water are performed under the condition that the maintenance of the aseptic condition in the cultivating chamber 14 can be surely prevented from being adversely affected.

The operation of the incubator 10a in the decontamination mode will be described with reference to a flowchart.

Figure 7:
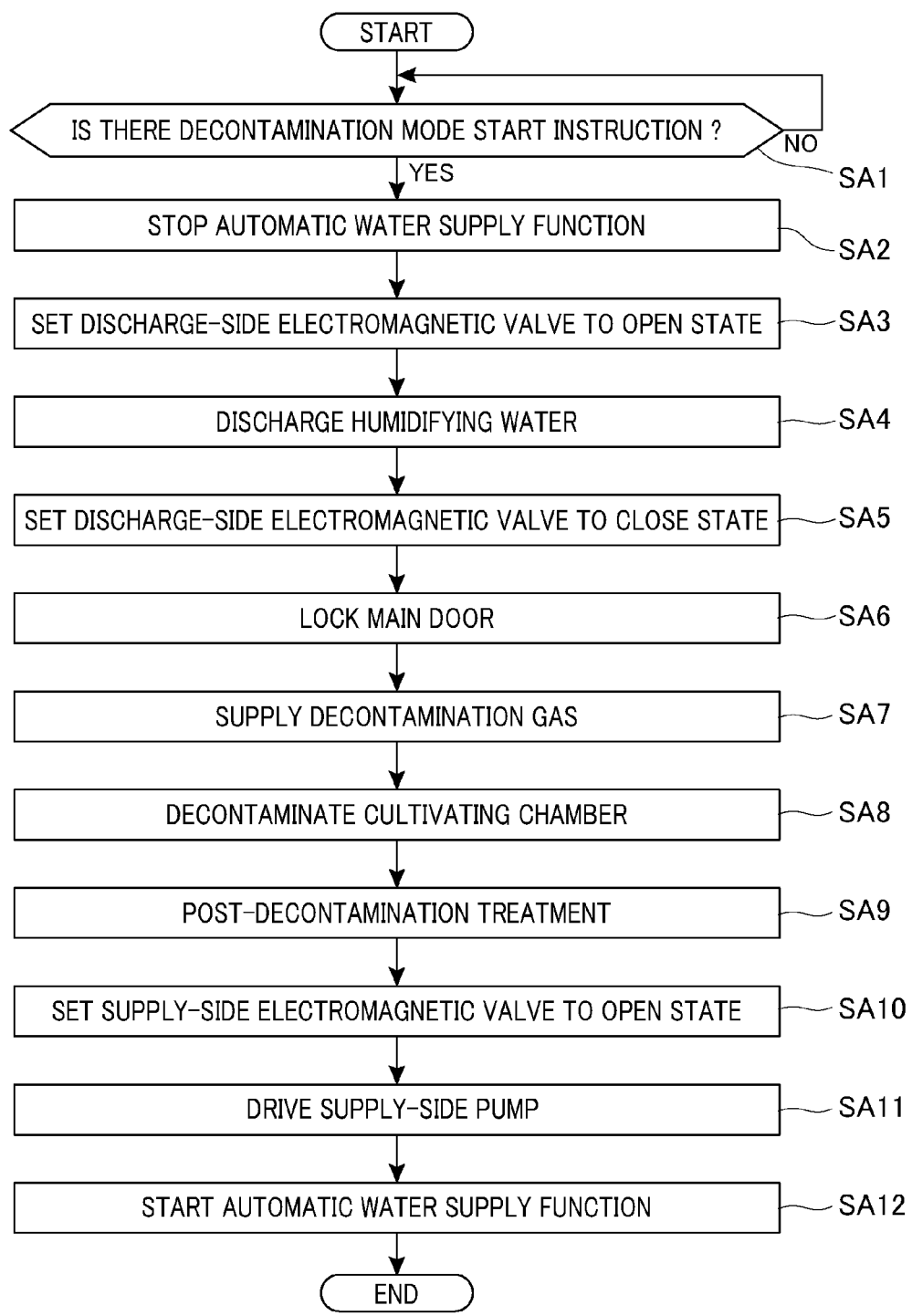
FIG. 7 is a flowchart showing the operation of the incubator.

FIG. 7 is a flowchart showing the operation of the incubator 10a in the decontamination mode.

The following flowchart is based on the assumption that the automatic water supply function is executed.

The automatic water supply function is executed so that the water level of humidifying water stocked in the humidifying water stock unit 32 is within a predetermined fixed range of the humidifying water stocked in the humidifying water stock unit 32. Specifically, when the automatic water supply function is executed, the controller 17 of the incubator 10a monitors on the basis of the detection value of the water level sensor 40 whether the water level of the humidifying water stock unit 32 exceeds a predetermined water level or not. The controller 17 sets the supply-side electromagnetic valve V1 to the close state and controls the supply-side pump P1 not to operate, thereby stopping supply of the humidifying water to the humidifying water stock unit 32 while the water level of the humidifying water stock unit 32 exceeds the predetermined water level.

On the other hand, when the water level of the humidifying water stock unit 32 is equal to or lower than the predetermined water level, the controller 17 sets the supply-side electromagnetic valve V1 to the open state and drives the supply-side pump P1 to supply only a predetermined amount of humidifying water from the water supply tank 34 into the humidifying water stock unit 32 so that the water level of the humidifying water stock unit 32 exceeds the predetermined water. As described above, when the automatic water supply function is executed, the water level of the humidifying water stocked in the humidifying water stock unit 32 is kept within the predetermined fixed range.

The following flowchart is based on the assumption that there are executed treatments/works required to execute the decontamination mode such as take-out of the cultures from the cultivating chamber 14, supplement of humidifying water in the water supply tank 34, supplement of hydrogen peroxide solution to the decontamination gas generating/removing unit 54, etc.

As shown in FIG. 7, the controller 17 of the incubator 10a determines whether a user instructs to start the decontamination mode (step SA1). The instruction of starting the decontamination mode is executed by executing a predetermined operation of instructing start of the decontamination mode on the operating switch 47.

When the start of the decontamination mode is instructed (step SA1: YES), the controller 17 stops the automatic water supply function (step SA2).

Subsequently, the controller 17 sets the discharge-side electromagnetic valve V2 to the open state (step SA3), discharges all the humidifying water stocked in the humidifying water stock unit 32 (step SA4), and sets the discharge-side electromagnetic valve V2 to the close state (step SA5) again. With respect to the discharge of all the humidifying water stocked in the humidifying water stock unit 32, a time period for which the discharge-side electromagnetic valve V2 should be kept to the open state to discharge all the humidifying water may be calculated in advance by a test or the like, and the discharge-side electromagnetic valve V2 may be set to the open state for the calculated time period or more. Alternatively, a dedicated sensor for detecting that all the humidifying water has been discharged may be provided, and the discharge-side electromagnetic valve V2 may be set to the open state on the basis of an output value of the sensor.

Subsequently, the controller 17 controls the locking device 16 to lock the main door (step SA6). In the following step, decontamination gas is supplied into the cultivating chamber 14. In this case, by locking the main door in step SA6, the main door is prevented from being opened while the decontamination gas is supplied into the cultivating chamber 14.

Subsequently, the controller 17 controls the decontamination gas generating/removing unit 54 and devices, equipment, etc. appendant to the unit 54 to generate atomized decontamination gas in the decontamination gas generating/removing unit 54, and supplies the generated decontamination gas into the cultivating chamber 14 (step SA7).

Subsequently, the controller 17 controls the decontamination gas generating/removing unit 54 and the devices, equipment, etc. appendant to the unit 54 to supply decontamination gas from the decontamination gas generating/removing unit 54 through the decontamination gas supply pipe 57 and the decontamination gas supply port 58 into the cultivating chamber 14, and also discharge decontamination gas through the decontamination gas discharging port 61 and the decontamination gas discharging pipe 60 into the decontamination gas generating/removing unit 54. Accordingly, the fan provided to the cultivating chamber 14 is driven so that atomized decontamination gas is filled over the whole area of the cultivating chamber 14 while the decontamination gas is circulated between the decontamination gas generating/removing unit 54 and the cultivating chamber 14, thereby decontaminating the cultivating chamber 14 (step SA8). The decontamination of the cultivating chamber 14 in step SA8 is continuously performed for only a predetermined time.

After the decontamination of the cultivating chamber 14 of the step SA8 is finished, the controller 17 executes a post-decontamination treatment containing a detoxifying treatment of decontamination gas executed by controlling the ultraviolet lamp, etc. provided in the cultivating chamber 14 to, etc. (step SA9).

Subsequently, the controller 17 sets the supply-side electromagnetic valve v1 to the open state (step SA10), and drives the supply-side pump P1 (step SA11) to start supply of humidifying water from the water supply tank 34 to the humidifying water stock unit 32, thereby executing the automatic water supply function (step SA12). Here, humidifying water flowing out from the water supply tank 34 is passed through the filter F1 and then supplied to the humidifying water stock unit 32. Accordingly, occurrence of such a situation that newly supplied humidifying water contains fungus and it adversely affects cultivation in the cultivating chamber 14 can be surely prevented.

As described above, in the incubator 10a according to this embodiment, humidifying water which is subjected to sterilization treatment by the filter F1 is automatically supplied under the state that the probability that fungus flows from the external into the cultivating chamber 14 after the decontamination of the cultivating chamber 14 is finished in the decontamination mode is interrupted. Accordingly, the discharge and supply of the humidifying water can be executed under the state that the aseptic condition of the cultivating chamber 14 is surely kept. Still furthermore, according to this embodiment, the discharge and supply of the humidifying water which are executed in connection with the decontamination of the cultivating chamber 14 are perfectly automated, and they are automatically performed by executing the decontamination mode. Accordingly, when the humidifying water is discharged or supplied, it is unnecessary for a user to execute a work of opening/closing the main door (the door for opening/closing the front opening of the cultivating chamber 14), etc., so that the working load imposed on the user can be reduced and the convenience for the user can be enhanced in connection with the reduction of the working load. Still furthermore, the working load imposed on the user can be surely prevented from adversely affecting the maintenance of the aseptic condition of the cultivating chamber 14.

As described above, in the incubator 10a according to this embodiment, the filter F1 is provided on the water supply pipe 35 for supplying humidifying water to the cultivating chamber 14.

Here, the filter F1 is a filter for sterilizing humidifying water passing through the filter F1 concerned. In this embodiment, a filter which can sterilize not only humidifying water, but also gas passing through the filter F1 is used as the filter F1. That is, the filter F1 sterilizes humidifying water passing therethrough, and also sterilizes gas passing therethrough.

As described above, according to this embodiment, the filter F1 for sterilizing humidifying water is provided on the water supply pipe 35. Accordingly, when humidifying water is supplied to the humidifying water stock unit 32, humidifying water containing fungus is prevented from being supplied to the humidifying water stock unit 32. Therefore, occurrence of a situation that the aseptic condition of the cultivating chamber 14 is adversely affected can be surely prevented. Furthermore, the filter F1 provided on the water supply pipe 35 has a function of sterilizing passing gas. Therefore, gas containing fungus can be surely prevented from flowing into the cultivating chamber 14 through the water supply pipe 35 from the upstream side of the filter F1 while no humidifying water is supplied. Accordingly, it can be expected that the aseptic condition of the cultivating chamber 14 is perfectly maintained.

Second Embodiment

Next, a second embodiment will be described.

Figure 8:
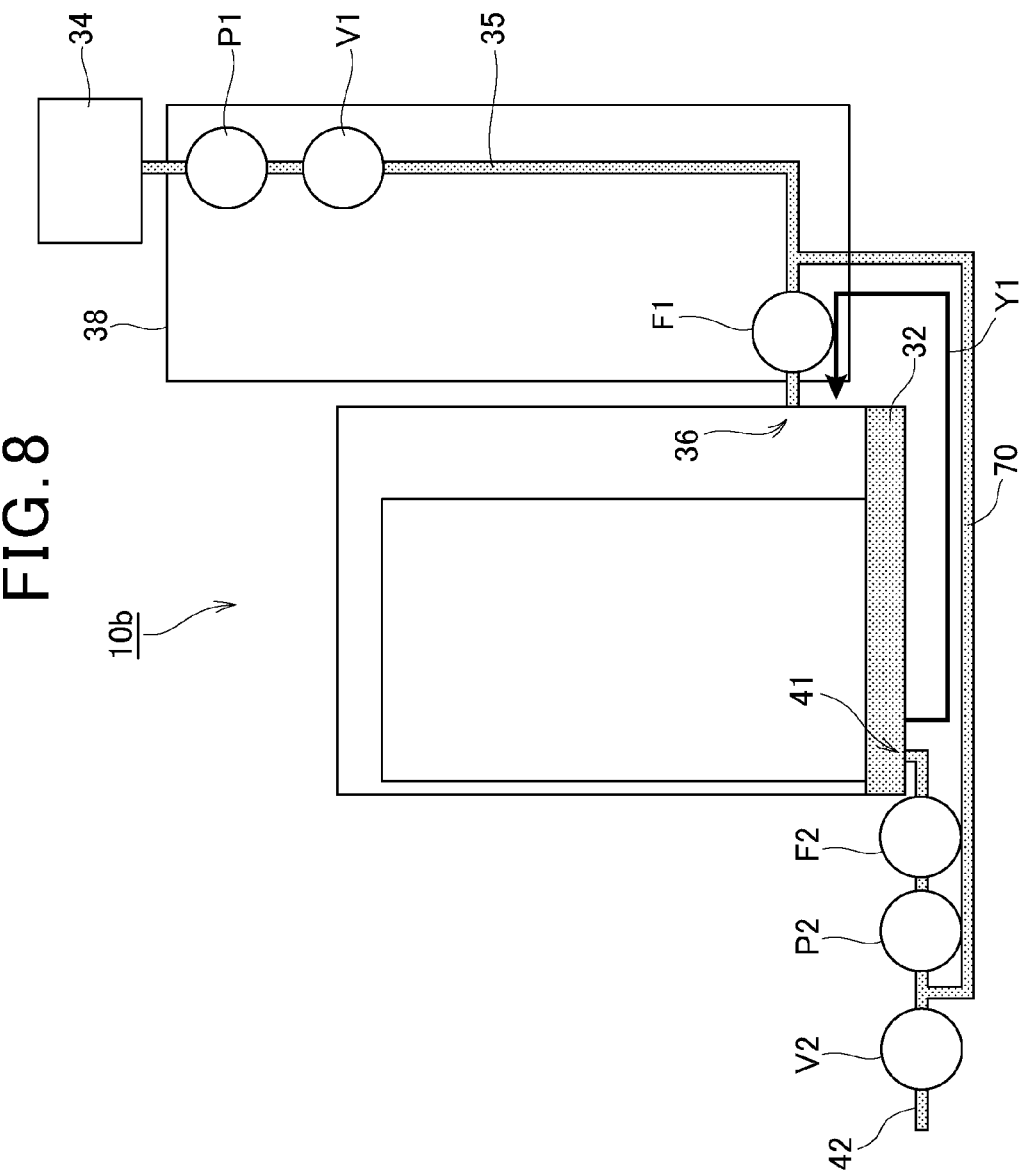
FIG. 8 is a diagram showing the construction of an incubator according to a second embodiment.

FIG. 8 is a diagram showing the construction of the incubator 10b according to the second embodiment.

In FIG. 8, the same constituent elements as shown in FIG. 5 are represented by the same reference numerals, and the description thereof is omitted.

As is apparent from the comparison between FIGS. 8 and 5, this embodiment is provided with a discharge-side filter F2 and a discharge-side pump P2 at the upstream side of the discharge-side electromagnetic valve V2.

The discharge-side filter F2 is a filter for sterilizing liquid and gas passing through the discharge-side filter F2. By providing the discharge-side filter F2 on the discharge water pipe 42, gas containing fungus can be surely prevented from flowing into the cultivating chamber 14 from the downstream side by the discharge-side filter F2.

The discharge-side pump P2 is a pump to be driven when humidifying water stocked in the humidifying water stock unit 32 is discharged. When humidifying water stocked in the humidifying water stock unit 32 is discharged, the discharge-side pump P2 is driven, and the humidifying water is sucked by the discharge-side pump P2, whereby pressure which enables humidifying water to flow through the discharge-side filter F2 at a predetermined flow rate is applied to the humidifying water.

One end of a first gas pipe 70 (gas passage) is connected to the discharge pipe 42 at the downstream side of the discharge-side pump P2 and at the upstream side of the discharge-side electromagnetic valve V2 (i.e., between the discharge-side pump P2 and the discharge-side electromagnetic valve V2). The other end of the first gas pipe 70 is connected to the water supply pipe 35 at the upstream side of the filter F1 and the downstream side of the supply-side electromagnetic valve V1 (i.e., between the filter F1 and the supply-side electromagnetic valve V1). As described in detail later, the first gas pipe 70 is a pipe through which decontamination gas flows in the decontamination mode.

Figure 9:
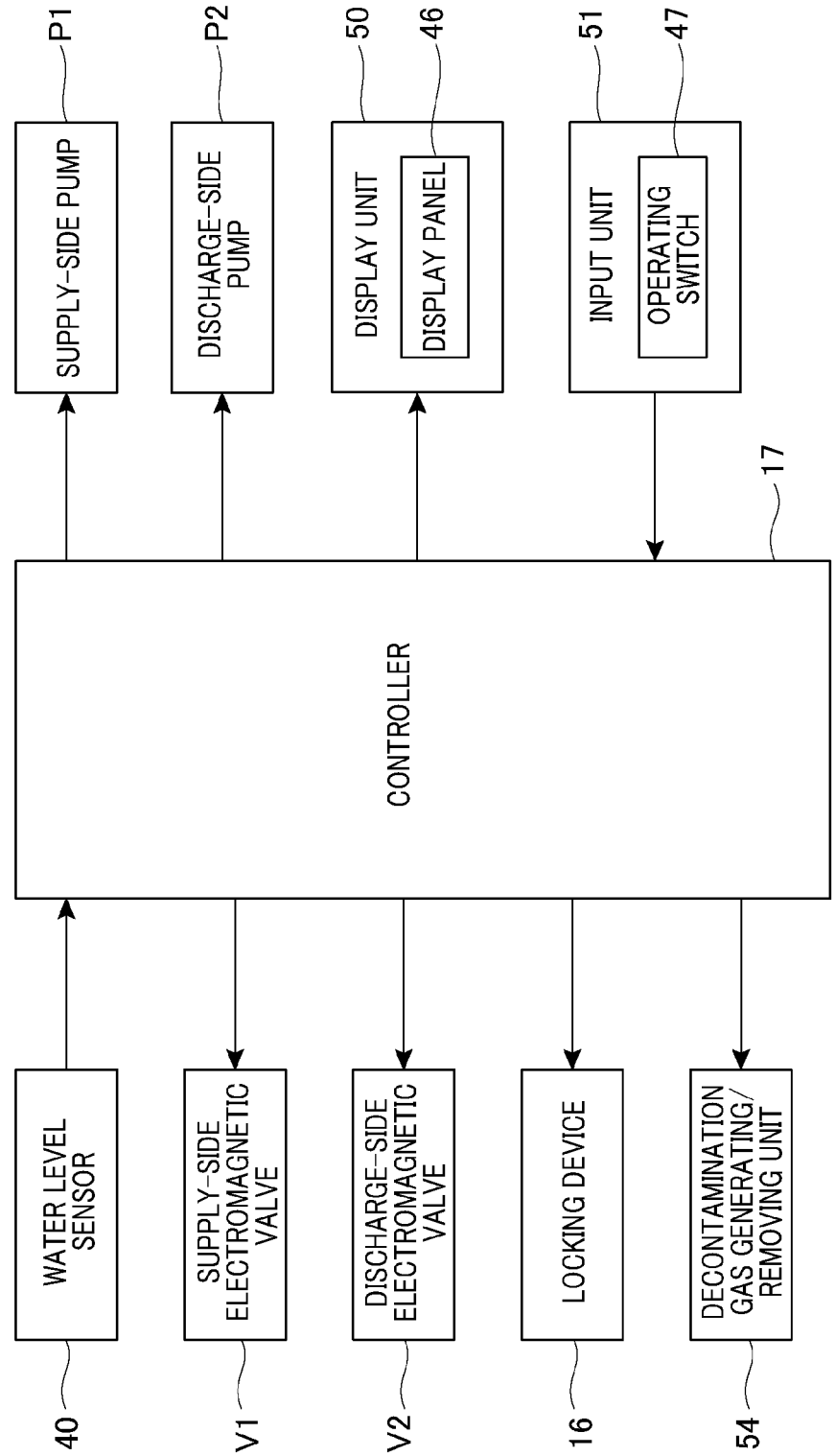
FIG. 9 is a diagram showing a functional construction of the incubator.

FIG. 9 is a block diagram showing the functional construction of the incubator 10b according to this embodiment.

In FIG. 9, the same constituent elements as shown in FIG. 6 are represented by the same reference numerals, and the description thereof is omitted.

As is apparent from the comparison between FIGS. 9 and 6, the discharge-side pump P2 is connected to the controller 17 according to this embodiment. The controller 17 controls the operation of the discharge-side pump P2.

Figure 10:
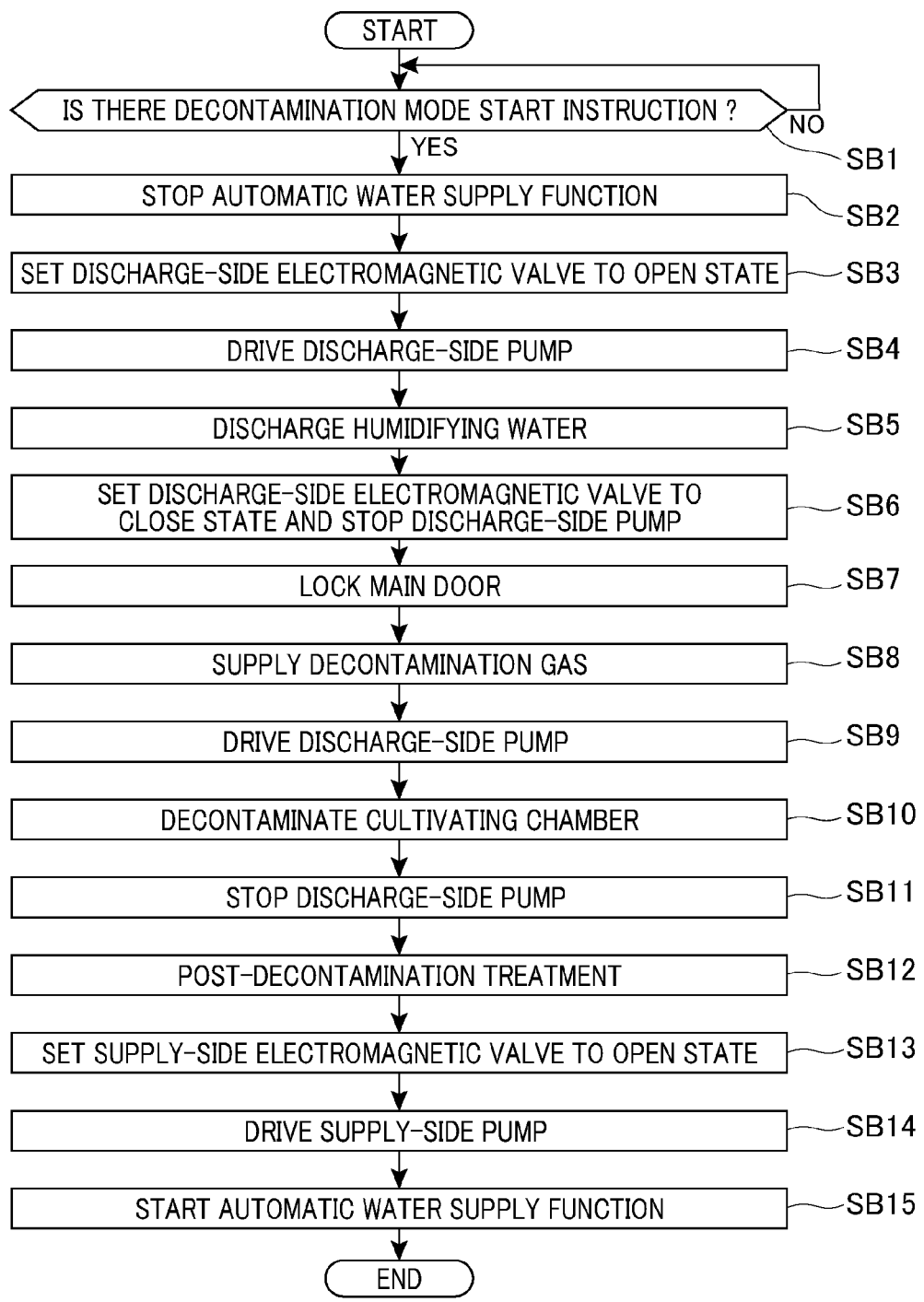
FIG. 10 is a flowchart showing the operation of the incubator.

FIG. 10 is a flowchart showing the operation of the incubator 10b according to this embodiment.

In the following operation, the controller 17 functions as an indoor decontaminating unit for supplying decontamination gas into the cultivating chamber 14 to decontaminate the inside of the cultivating chamber 14, and a passage decontaminating unit for decontaminating the water supply pipe 35 as the water supply passage and the water discharge pipe 42 as the water discharge passage by using the decontamination gas supplied to the cultivating chamber 14.

First, in steps SB1 to SB3, the same processing as the steps SA1 to SA3 of FIG. 7 is executed.

After the processing of the step SB3 is executed, the controller 17 drives the discharge-side pump P2 (step SB4) to discharge humidifying water stocked in the humidifying water stock unit 32 (step SB5). As described above, according to this embodiment, the discharge-side filter F2 is provided on the water discharge pipe 42, and thus humidifying water stocked in the humidifying water stock unit 32 can be discharged by driving the discharge-side pump P2.

After the humidifying water stocked in the humidifying water stock unit 32 is discharged, the controller 17 sets the discharge-side electromagnetic valve V2 to the close state, and also stops the driving of the discharge-side pump P2 (step SB6). Subsequently, the controller 17 controls the locking device 16 to lock the main door (step SB7).

Subsequently, the controller 17 controls the decontamination gas generating/removing unit 54 and the devices, equipment, etc. appendant to the unit 54 to generate atomized decontamination gas in the decontamination gas/removing unit 54, and supplies the generated decontamination gas to the cultivating chamber 14 (step SB8).

Subsequently, the controller 17 drives the discharge-side pump P2 (step SB9). By driving the discharge-side pump P2 in this step SB9, the decontamination gas supplied to the cultivating chamber 14 is sucked by the discharge-side pump P2 to flow into the water discharge pipe 42 through the water discharge port as indicated by an arrow Y1 of FIG. 8, and also the decontamination gas flowing into the water discharge pipe 42 passes through the first gas pipe 70 and the water supply pipe 35 and flows into the cultivating chamber 14 through the water supply port 36 again. As describe above, the decontamination gas flows into the water discharge pipe 42, the first gas pipe 70 and the water supply pipe 35, whereby the inside of these pipes are decontaminated by the decontamination gas and it is sure to maintain the aseptic condition of the cultivating chamber 14. Particularly, according to this embodiment, through the flow of the decontamination gas through these pipes, the decontamination gas is filled between the filter F1 and the water supply port 36 and between the discharge-side filter F2 and the water discharge port 41, whereby the decontamination of these areas is surely performed and the maintenance of the aseptic condition of the cultivating chamber 14 can be made sure.

Subsequently, the controller 17 controls the decontamination gas generating/removing unit 54 and the devices, equipment, etc. appendant to the unit 54 to supply decontamination gas to the from the decontamination gas generating/removing unit 54 through the decontamination gas supply pipe 57 and the decontamination gas supply port 58 to the cultivating chamber 14, and also discharges the decontamination gas through the decontamination gas discharge port 61 and the decontamination gas discharge pipe 60 into the decontamination gas generating/removing unit 54. Accordingly, the fan provided to the cultivating chamber 14 is driven while the decontamination gas is circulated between the decontamination gas generating/removing unit 54 and the cultivating chamber 14, whereby the atomized decontamination gas is made to prevail over the whole area of the cultivating chamber 14, thereby decontaminating the inside of the cultivating chamber 14 (step SB10). The decontamination of the cultivating chamber 14 in this step SB10 is repeated for a predetermined time period.

Subsequently, the controller 17 stops the operation of the discharge-side pump P2 to stop the flow of the decontamination gas into the water discharge pipe 42, the first gas pipe 70 and the water supply pipe 35 (step SB11).

Subsequently, the same processing as the steps SA9 to SA12 of FIG. 7 is executed in steps SB12 to SB15.

As described above, according to this embodiment, the controller 17 functions as the indoor decontaminating unit for decontaminating the inside of the cultivating chamber 14 by supplying the decontamination gas to the cultivating chamber 14 and the passage decontaminating unit for decontaminating the inside of the water supply pipe 35 by using the decontamination gas supplied to the cultivating chamber 14.

Accordingly, the decontamination in the water supply pipe 35 can be implemented, and the aseptic condition of the cultivating chamber 14 can be surely maintained. Particularly, in this embodiment, the decontamination of the inside of the water supply pipe 35 can be performed by using the decontamination gas supplied to the cultivating chamber 14, and thus it is unnecessary to provide special facilities and a special step for decontaminating the water supply pipe 35.

In this embodiment, the controller 17 functioning as the passage decontaminating unit further decontaminating the water discharge pipe 42 for discharging water stocked in the cultivating chamber 14 by using the decontamination gas supplied to the cultivating chamber 14.

Accordingly, the decontamination of the inside of the water discharge pipe 42 can be implemented, and the aseptic condition of the cultivating chamber 14 can be surely maintained. Particularly, in this embodiment, the decontamination of the inside of the water discharge pipe 42 can be performed by using the decontamination gas supplied to the cultivating chamber 14, and thus it is unnecessary to provide special facilities and a special step for decontaminating the water discharge pipe 42.

Furthermore, the incubator 10b according to this embodiment is provided with the first gas pipe 70 which is connected to the upstream side of the water supply pipe 35 with respect to the locating position of the filter F1 at one end thereof and also connected to the water discharge pipe 42 at the other end thereof. The controller 17 functioning as the passage decontaminating unit drives the discharge-side pump P2 to suck the decontamination gas supplied to the cultivating chamber 14 from the water discharge port 41 and circulate the water discharge port 41, the first gas pipe 70 and the water supply port 36 in this order, thereby executing the decontamination of the insides of these pipes.

Accordingly, the decontamination of these pipes can be surely performed by using the decontamination gas supplied to the cultivating chamber 14, and the aseptic condition of the cultivating chamber 14 can be surely maintained. Particularly, in this embodiment, the decontamination gas flows through these pipes, whereby the decontamination gas is made to prevail between the filter F1 and the water support port 36 and between the discharge-side filter F2 and the water discharge port 41. Therefore, these portions are surely decontaminated, and the aseptic condition of the cultivating chamber 14 can be more surely maintained.

Third Embodiment

Next, a third embodiment will be described.

Figure 11:
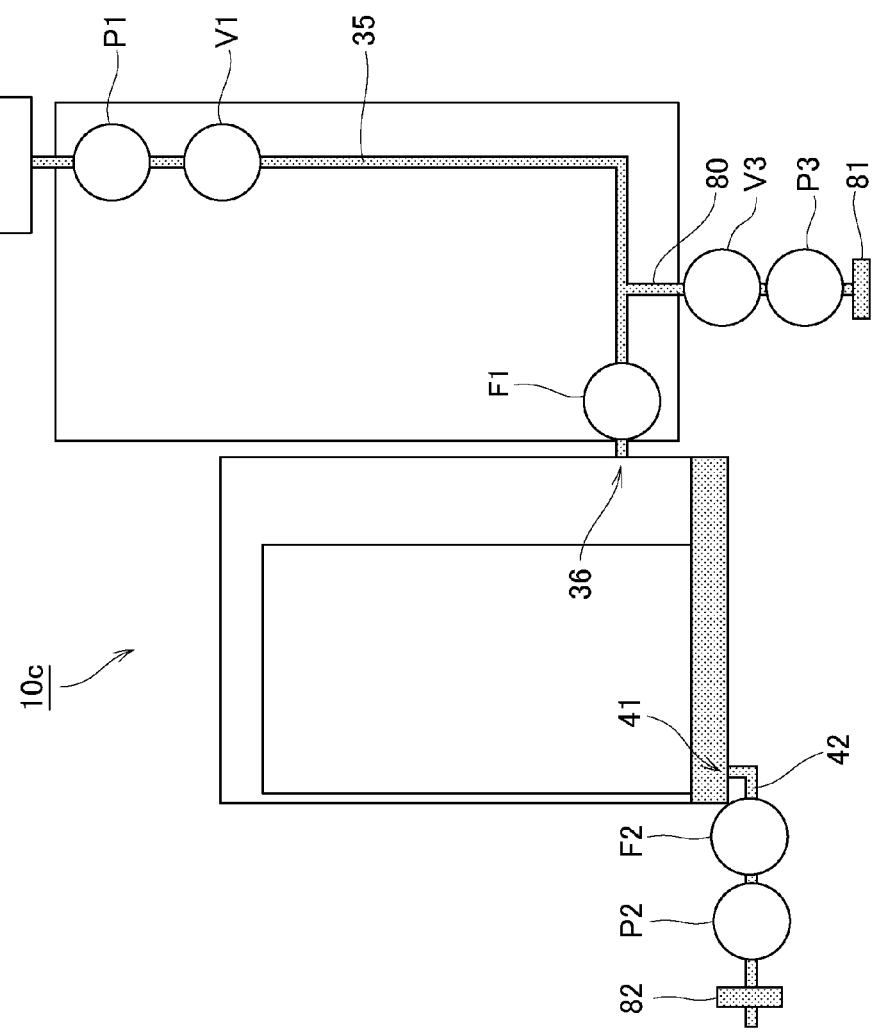
FIG. 11 is a diagram showing the construction of the incubator according to a third embodiment.

FIG. 11 is a diagram showing the construction of an incubator 10c according to the third embodiment.

In FIG. 11, the same constituent elements as shown in FIG. 5 are represented by the same reference numerals, and the description thereof is omitted.

As is apparent from the comparison between FIGS. 11 and 5, in this embodiment, one end of a second gas pipe 80 (gas passage) is connected to the water supply pipe 35 at the upstream side of the filter F1 and at the downstream side of the supply-side electromagnetic valve V1 (i.e., between the filter F1 and the supply-side electromagnetic valve V1). The other end of the second gas pipe 80 is connected to a gas discharge portion 81. The gas discharge portion 81 has a function of rendering the decontamination gas harmless by using platinum catalyst, irradiation of ultraviolet rays or the like and discharging the harmless decontamination gas to the outside. A third electromagnetic valve V3 and a third pump P3 are provided on the second gas pipe 80 from the upstream side in this order.

As in the case of the second embodiment described above, the discharge-side filter F2 and the discharge-side pump P2 are provided on the water discharge pipe 42, and also a second gas discharge portion 82 is provided at the downstream side of the discharge-side pump P2 on the water discharge pipe 42. As in the case of the gas discharge portion 81 described above, the second gas discharge portion 82 has a function of rendering the decontamination gas harmless by using platinum catalyst, irradiation of ultraviolet rays or the like and discharging the harmless decontamination gas to the outside.

Figure 12:
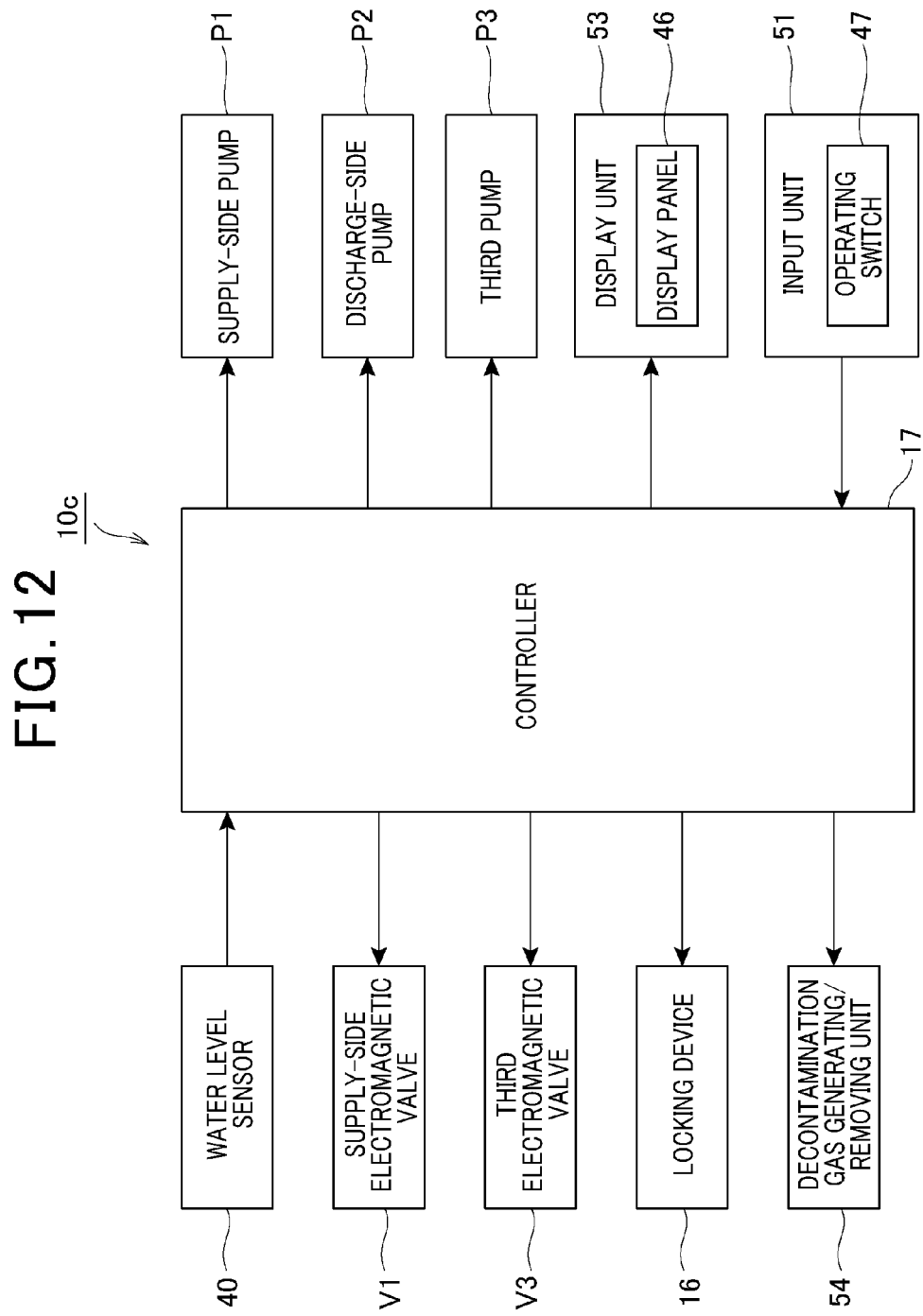
FIG. 12 is a diagram showing a functional construction of the incubator.

FIG. 12 is a block diagram showing the functional construction of the incubator 10c according to this embodiment.

In FIG. 12, the same constituent elements as shown in FIG. 6 are represented by the same reference numerals, and the description thereof is omitted.

As is apparent from the comparison between FIGS. 12 and 6, the controller 17 of this embodiment is connected to the discharge-side pump P2 and the third pump P3. The controller 17 controls the operation of these pumps. A third electromagnetic valve V3 is connected to the controller 17, and the controller 17 controls the opening/closing operation of the third electromagnetic valve V3.

Figure 13:
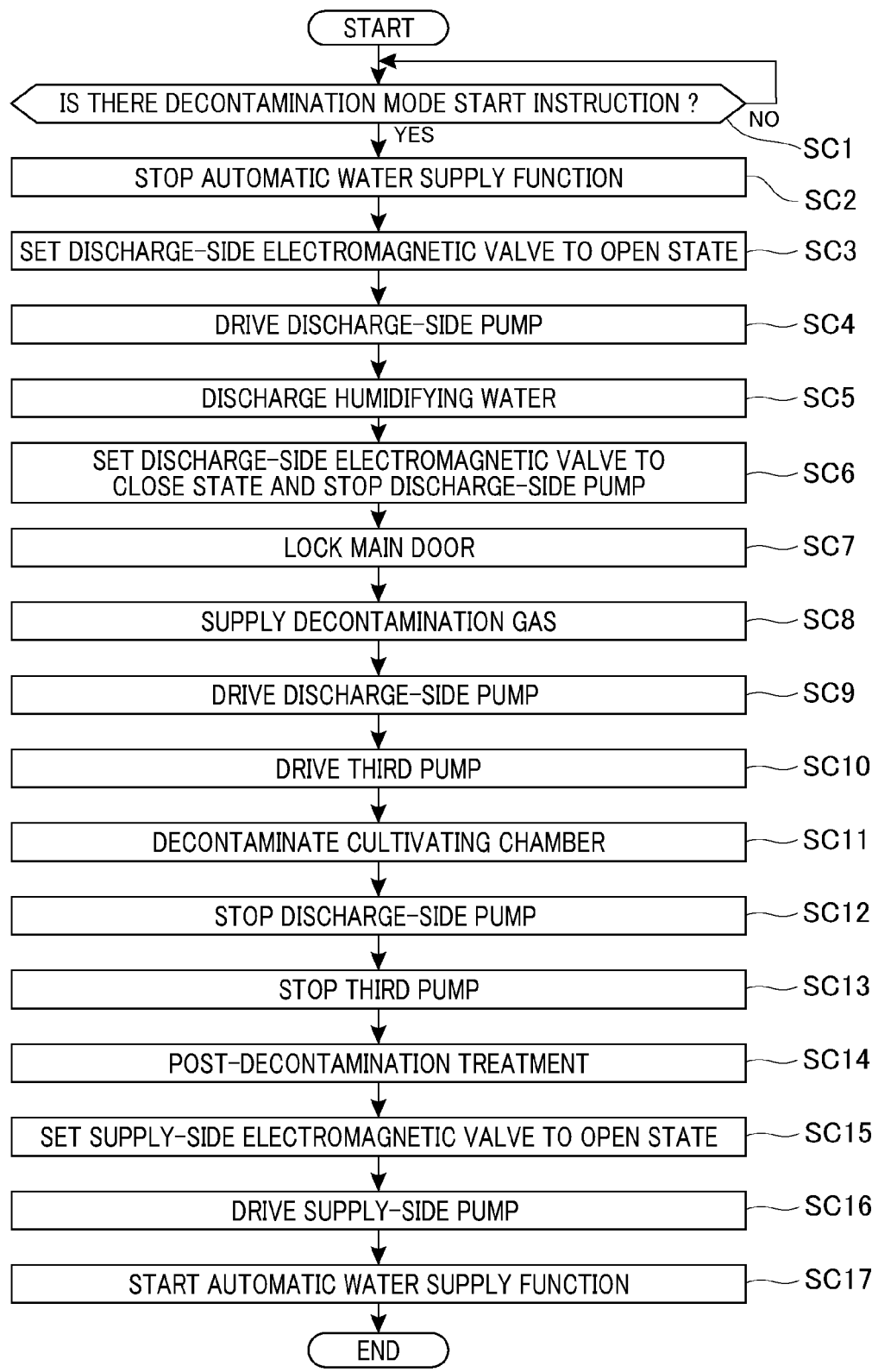
FIG. 13 is a flowchart showing the operation of the incubator.

FIG. 13 is a flowchart showing the operation of the incubator 10c according to this embodiment.

In the following operation, the controller 17 functions as the indoor decontaminating unit for supplying decontamination gas into the cultivating chamber 14 to decontaminate the inside of the cultivating chamber 14, and the passage decontaminating unit for decontaminating the water supply pipe 35 as the water supply passage and the water discharge pipe 42 as the water discharge passage by using the decontamination gas supplied to the cultivating chamber 14.

In steps SC1 to SSC8, the same processing as the steps SA1 to SA8 of FIG. 10 is executed.

In step SC9, the controller 17 drives the discharge-side pump P2. Accordingly, decontamination gas supplied to the cultivating chamber 14 flows into the water discharge pipe 42, and it is rendered harmless in the second gas discharge portion 82 and then discharged to the outside. Therefore, the water discharge pipe 42 is decontaminated by the decontamination gas flowing into the water discharge pipe 42, and the aseptic condition of the cultivating chamber 14 is surely maintained. Particularly, in this embodiment, the decontamination between the water discharge port 41 of the water discharge pipe 42 and the discharge-side filter F2 is surely performed by the processing of the step SC9, and the aseptic condition of the cultivating chamber 14 is more surely maintained.

Subsequently, the controller 17 sets the third electromagnetic valve V3 to the open state, and then drives the third pump P3 (step SC10). accordingly, the decontamination gas supplied to the cultivating chamber 14 flows into the water supply pipe 35, and it is rendered harmless in the gas discharge portion 81 and then discharged to the outside. Therefore, the water supply pipe 35 is decontaminated by the decontamination gas flowing into the water discharge pipe 42, and the aseptic condition of the cultivating chamber 14 is surely maintained. Particularly, in this embodiment, the decontamination between the water supply port 36 of the water supply pipe 35 and the filter F1 is surely performed, and the aseptic condition of the cultivating chamber 14 is more surely maintained.

Subsequently, the controller 17 controls the decontamination gas generating/removing unit 54 and the devices, equipment, etc. appendant to the unit 54 so that the decontamination gas is supplied from the decontamination gas generating/removing unit 54 through the decontamination gas supply pipe 57 and the decontamination gas supply port 58 into the cultivating chamber 14 and also the decontamination gas is discharged through the decontamination gas discharge port 61 and the decontamination gas discharge pipe 60 to the decontamination gas generating/removing unit 54. Accordingly, the fan provided to the cultivating chamber 14 is driven while the decontamination gas is circulated between the decontamination gas generating/removing unit 54 and the cultivating chamber 14, thereby making the atomized decontamination gas prevail over the whole area of the cultivating chamber 14 and decontaminating the cultivating chamber 14 (step SC11). The decontamination of the cultivating chamber 14 in the step SC11 is continued for only a predetermined time.

Subsequently, the controller 17 stops the operation of the discharge-side pump P2 to stop flow-in of the decontamination gas into the water discharge pipe 42 (step SC12).

Subsequently, the controller 17 sets the third electromagnetic valve V3 to the close state and stops the operation of the third pump P3, thereby stopping flow-in of the decontamination gas into the water supply pipe 35 (step SC13).

Subsequently, in the steps SC14 to SC17, the same processing as the steps sB12 to SB15 of FIG. 10 is executed.

As described above, the incubator 10c according to this embodiment is provided with the second gas pipe 80. One end of the gas pipe 80 is connected to the upstream side of the locating position of the filter F1 provided in the water supply pipe 35, and also the other end of the gas pipe 80 is connected to the gas discharge portion 81 which can discharge gas to the outside. Furthermore, the incubator 10c is provided with the third pump P3 on the second gas pipe 80. The third pump P3 is used to suck decontamination gas from the water supply port 36 formed at the end portion of the water supply pipe 35 at the cultivating chamber side and discharge the decontamination gas through the water supply pipe 35 and the second gas pipe 80 into the gas discharge portion 81. The controller 17 functioning as the passage decontaminating unit drives the third pump P3 to suck the decontamination gas supplied to the cultivating chamber from the water supply port 36, and discharge the decontamination gas through the water supply pipe 35 and the second gas pipe 80 into the gas discharge portion 81, thereby decontaminating the inside of the water supply pipe 35.

Accordingly, the decontamination of the water supply pipe 35 can be surely performed by using the decontamination gas supplied to the cultivating chamber 14, and the aseptic condition of the cultivating chamber 14 can be surely maintained. Particularly, according to this embodiment, the decontamination between the water supply port 36 of the water supply pipe 35 and the filter F1 can be surely performed, and the aseptic condition of the cultivating chamber 14 can be further surely maintained.

Fourth Embodiment

Next, a fourth embodiment will be described.

Figure 14:
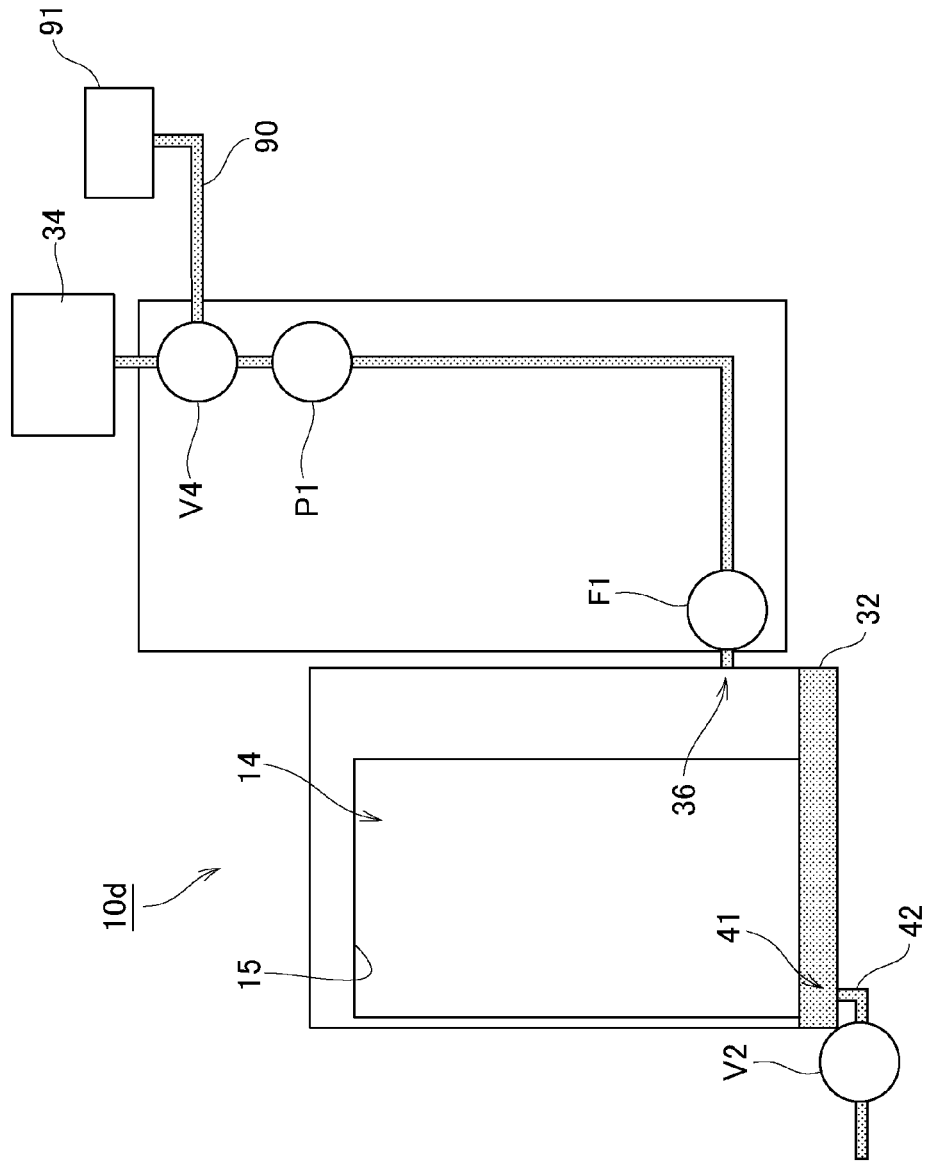
FIG. 14 is a diagram showing the construction of an incubator according to a fourth embodiment.

FIG. 14 is a diagram showing the construction of an incubator 10d according to the fourth embodiment.

In FIG. 14, the same constituent elements as shown in FIG. 5 are presented by the same reference numerals, and the description thereof is omitted.

As is apparent from the comparison between FIGS. 14 and 5, this embodiment is provided with a supply-side electromagnetic valve V4 at the upstream side of the supply-side pump P1 on the water supply pipe 35. One end of a decontamination liquid supply pipe 90 (decontamination liquid supply passage) is connected to the supply-side electromagnetic valve V4, and the other end of the decontamination liquid supply pipe 90 is connected to a decontamination liquid tank 91. The decontamination liquid tank 91 is a tank for stocking hydrogen peroxide solution as decontamination liquid.

Here, the supply-side electromagnetic valve V4 according to this embodiment comprises a three-way valve. The valve at the water supply tank 34 side is set to the open state to make humidifying water flow from the water supply tank 34 through the water supply pipe 35 to the water supply port 36, and the valve at the decontamination liquid tank 91 side to the open state to make decontamination liquid from the decontamination liquid through the water supply pipe 35 to the water supply port 36. Furthermore the above two valves are set to the close state to stop the flow of the humidifying water and the decontamination liquid to the water supply port 36.

Figure 15:
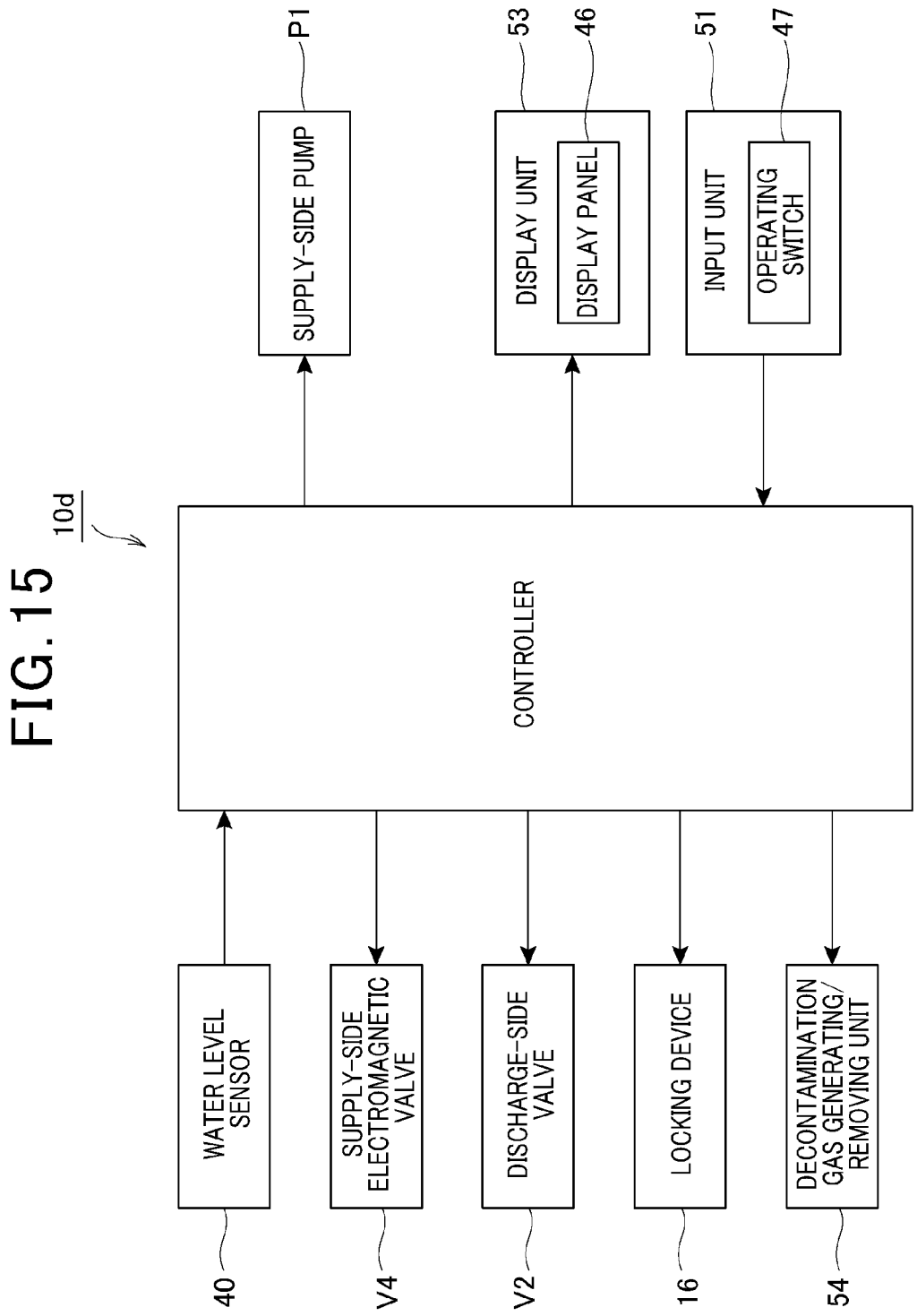
FIG. 15 is a diagram showing a functional construction of the incubator.

FIG. 15 is a block diagram showing the functional construction of the incubator 10c according to this embodiment.

In FIG. 15, the same constituent elements as shown in FIG. 6 are represented by the same reference numerals, and the description thereof is omitted.

As is apparent from the comparison between FIGS. 15 and 6, the supply-side electromagnetic valve V4 is connected to the controller 17 according to this embodiment. The controller 17 controls the opening/closing operation of the supply-side electromagnetic valve V4.

Figure 16:
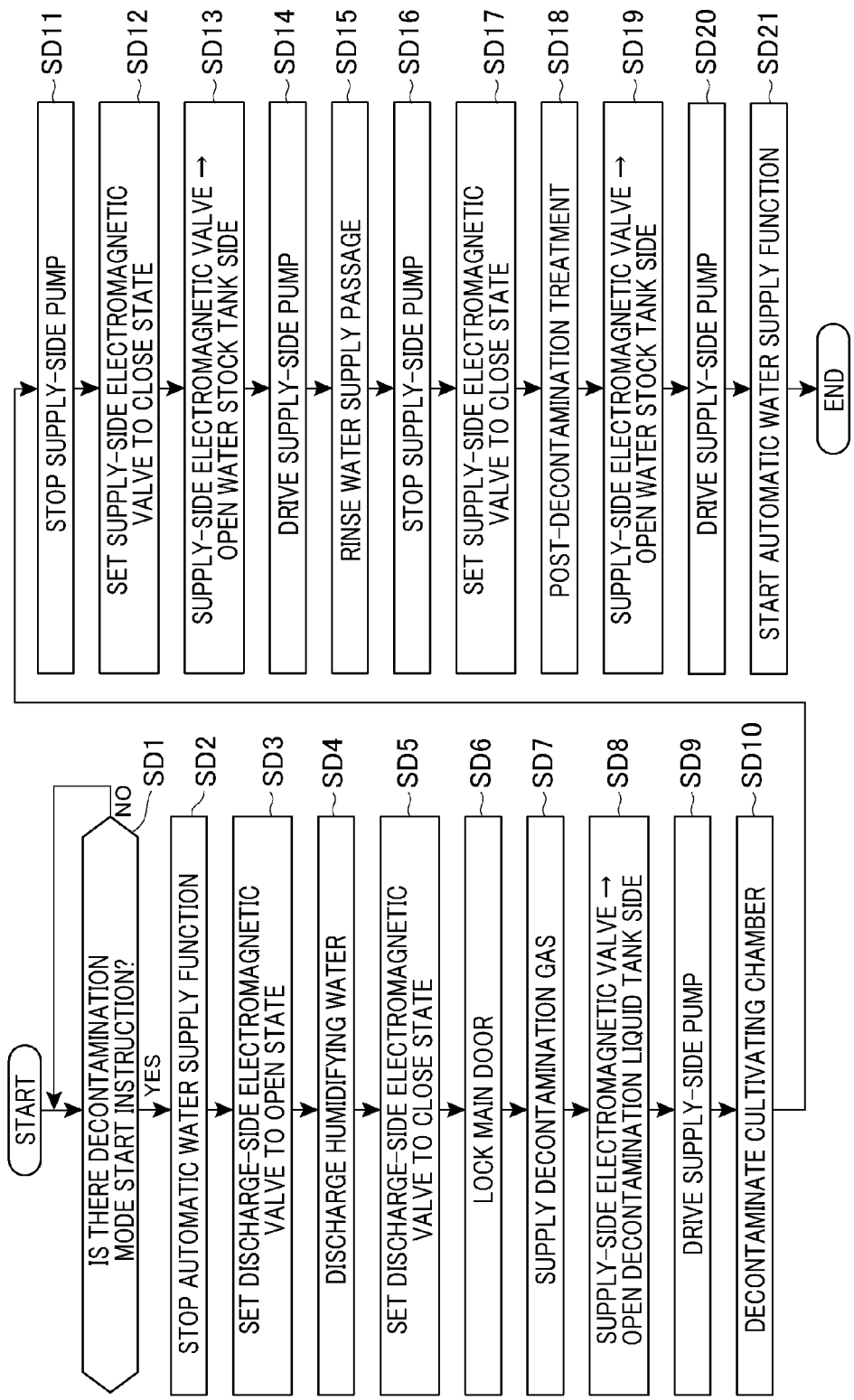
FIG. 16 is a flowchart showing the operation of the incubator.

FIG. 16 is a flowchart showing the operation of the incubator 10d according to this embodiment.

In the following operation, the controller 17 functions as the indoor decontaminating unit for supplying decontamination gas to the cultivating chamber 14 to decontaminate the inside of the cultivating chamber 14, and the passage decontaminating unit for decontaminating the water supply pipe 35 as the water supply passage and the water discharge pipe 42 as the water discharge passage by using the decontamination gas supplied to the cultivating chamber 14.

First, in the steps SD1 to SD7, the same processing as the steps SA1 to SA7 of FIG. 7 is executed.

After the processing of the step SD7 is executed, the controller 17 sets the decontamination liquid tank 91 side of the supply-side electromagnetic valve V4 to the open state (step SD8), whereby the decontamination liquid stocked in the decontamination liquid tank 91 can flow through the water supply pipe 35 into the water supply port 36.

Subsequently, the controller 17 drives the supply-side pump P1 (step SD9). By driving the supply-side pump P1 in step SD9, the decontamination liquid stocked in the decontamination liquid tank 91 passes through the decontamination liquid supply pipe 90 and the water supply pipe 35 and flows through the water supply port 36 into the cultivating chamber 14. As described above, the decontamination liquid flows through the decontamination liquid supply pipe 90 and the water supply pipe 35, whereby these pipes are decontaminated and the aseptic condition of the cultivating chamber 14 can be surely maintained. Particularly, in this embodiment, the decontamination liquid flows through these pipes, whereby the decontamination liquid is made to prevail between the filter f1 and the water supply port 36 in the water supply pipe 35. Therefore, the these portions are surely decontaminated, and the aseptic condition of the cultivating chamber 14 is more surely maintained.

Subsequently, the controller 17 controls the decontamination gas generating/removing unit 54 and the devices, equipment, etc. appendant to the unit 54 to supply the decontamination gas from the decontamination gas generating/removing unit 54 through the decontamination gas supply pipe 57 and the decontamination gas supply port 58 into the cultivating chamber 14, and also discharging the decontamination gas through the decontamination gas discharge port 61 and the decontamination gas discharge pipe 60 into the decontamination gas generating/removing unit 54. Accordingly, the fan provided to the cultivating chamber 14 is driven while the decontamination gas is circulated between the decontamination gas generating/removing unit 54 and the cultivating chamber 14, whereby the atomized decontamination gas is made to prevail over the whole area of the cultivating chamber 14 and the cultivating chamber 14 is decontaminated (step SD10). The decontamination of the cultivating chamber 14 in step SD 10 is continued for only a predetermined time.

Subsequently, the controller 17 stops the driving of the supply-side pump P1 (step SD11), and also sets the supply-side electromagnetic valve V4 to the close state (step SD12), whereby the decontamination liquid stocked in the decontamination liquid tank 91 is stopped to flow into the decontamination supply pipe 90.

Subsequently, the controller 17 sets the water supply tank 34 side of the supply-side electromagnetic valve V4 to the open state (step SD13), whereby humidifying water stocked in the water supply tank 34 is allowed to flow through the water supply pipe 35 into the water supply port 36.

Subsequently, the controller 17 drives the supply-side pump P1 (step SD14). By driving the supply-side pump P1 in step SD14, the humidifying water stocked in the water supply tank 34 flows through the water supply pipe 35 and the water supply port 36 into the cultivating chamber 14. Accordingly, the water supply pipe 35 is cleaned, and the decontamination liquid remaining in the water supply pipe 35 is removed from the water supply pipe 35 (step SD15). The removable of the decontamination liquid remaining in the water supply pipe 35 is executed for a predetermined time.

Subsequently, the controller 17 stops the driving of the supply-side pump P1 (step SD16), and also sets the supply-side electromagnetic valve V4 to the close state (step SD17), thereby stopping flow-in of the humidifying water stocked in the water supply pipe 35.

Subsequently, the controller 17 executes the post-decontamination treatment which follows the discharge of the liquid stocked in the humidifying water stock unit 32 (the humidifying water supplied to clean the water supply pipe 35 in step SD15) which is caused by making the decontamination gas harmless and also setting the discharge-side electromagnetic valve V2 to the open state (step SD18).

Subsequently, in steps SD19 to SD21, the same processing as the steps SA10 to SA12 of FIG. 7 is executed.

As described above, the incubator 10d according to this embodiment is provided with a decontamination liquid supply pipe 90 and a fourth pump P4. On end of the decontamination liquid supply pipe 90 is connected to the upstream side of the locating position of the filter F1 in the water supply pipe 35, and the other end thereof is connected to the decontamination liquid tank 91 for stocking decontamination liquid. The fourth pump P4 is provided on the decontamination liquid supply pipe 90 so as to make the decontamination liquid flow from the decontamination liquid tank 91 through the decontamination liquid supply pipe 90 and the water supply pipe 35 to the water supply port 36 formed at the end portion of the cultivating chamber 14 side of the water supply pipe 35.

The controller 17 functioning as the passage decontaminating unit drives the fourth pump P4 to make the decontamination liquid flow from the decontamination liquid tank 91 through the decontamination liquid supply pipe 90 and the water supply pipe 35 to the water supply port 36 formed at the end portion of the cultivating chamber 14 side of the water supply pipe 35, thereby decontaminating the water supply pipe 35.

Accordingly, by using the decontamination liquid stocked in the decontamination liquid tank 91, the decontamination of the water supply pipe 35 can be surely performed, and the aseptic condition of the cultivating chamber 14 can be surely maintained. Particularly, according to this embodiment, the decontamination between the water supply port 36 of the water supply pipe 35 and the filter F1 can be surely performed, and the aseptic condition of the cultivating chamber 14 can be further surely maintained.

The present invention is not limited to the above-described embodiments, and various modifications and application can be made without departing from the subject matter of the present invention.

For example, in the above embodiments, the incubators 10a, 10b, 10c, 10d have the automatic feeder 20. However, the present invention may be applied to an incubator having no automatic feeder 20. That is, the present invention may be applied to any incubator which supplies humidifying water to the cultivating chamber 14 and adjusts the humidity in the cultivating chamber by the humidifying water. Furthermore, in the above embodiments, the automatic feeder 20 is designed to have the grip portion 22 as the automatic feeder 20. However, the automatic feeder 20 is not limited to the above type, and it may be designed as such a type that it moves in the front-and-rear direction and the right-and-left direction while the containers 19 are mounted thereon.

Furthermore, in the above embodiments, the decontamination gas generating/removing unit 54 atomizes hydrogen peroxide solution (or hydrogen peroxide water) by ultrasonic waves to generate decontamination gas. However, hydrogen peroxide solution (water) may be heated and vaporized to generate decontamination gas. Furthermore, decontamination gas may be generated from hydrogen peroxide solution (water) by using both ultrasonic waves and heating vaporization.

Still furthermore, in the above embodiments, the incubators 10a, 10b, 10c, 10d are used while joined to the isolator 11. However, the using style of the incubator is not limited to the above embodiments. For example, the incubator may be used while joined to a biohazard-adaptable cabinet or the like which can decontaminate the inside of the incubator 10a, 10b, 10c, 10d and can be joined through a joint portion 27 to the incubator 10a, 10b, 10c, 10d. Furthermore, the incubator 10a, 10b, 10c, 10d may be used alone. In these cases, the incubator may be combined with a decontaminating unit suitable for each case, whereby the decontamination function can be brought to make the present invention applicable.

Still furthermore, in the above embodiments, the controller 17 having the incubator 10a, 10b, 10c, 10d controls the decontamination gas generating/removing unit 54, etc. to execute the decontamination function of decontaminating the cultivating chamber 14. However, the method of executing the decontaminating function is not limited to the above embodiment. For example, a control mechanism may be provided to the decontaminating unit so that the control mechanism and the controller 17 is connected to each other so as to be communicable therebetween, whereby the control mechanism and the controller 17 execute the decontamination function in cooperation with each other.

Furthermore, in FIGS. 5, 8 and 11, the supply-side electromagnetic valve V1 is provided at the downstream side of the supply-side pump P1 in the water supply pipe 35. Conversely, the supply-side pump P1 may be provided at the downstream side of the supply-side electromagnetic valve V1. Furthermore, in FIG. 11, the third pump P3 is provided at the downstream side of the third electromagnetic valve V3 in the second gas pipe 80. Conversely, the third electromagnetic valve V3 may be provided at the downstream side of the third pump P3.

In the above embodiments, a target to be sterilized is "fungus". However, the present invention is not limited to "fungus", and various microorganisms such as virus, bacteria, etc. may be targeted in addition to "fungus".

What is claimed is:

1. An incubator, comprising:
    a cultivating chamber for cultivating cultures;
    a water supply control unit for supplying water into the cultivating chamber through a water supply passage and adjusting the humidity of the inside of the cultivating chamber; and
    a filter provided in the water supply passage,
    wherein the water supply control unit comprises:
        an indoor decontaminating unit for supplying decontamination gas into the cultivating chamber to decontaminate the inside of the cultivating chamber, and
        a passage decontaminating unit for decontaminating the inside of the water supply passage by using the decontamination gas supplied to the cultivating chamber by the indoor decontaminating unit.

2. The incubator according to claim 1, further comprising a water discharge passage for discharging water stocked in the cultivating chamber,
    wherein the passage decontaminating unit further decontaminates the inside of the water discharge passage by using decontamination gas supplied to the cultivating chamber by the indoor decontaminating unit.

3. The incubator according to claim 2, further comprising:
a first gas passage connected to an upstream side of the filter in the water supply passage at one end thereof, and to the water discharge passage at the other end thereof, and
a first pump provided on a first passage, the first passage extending from a water discharge port formed at an end portion at the cultivating chamber side of the water discharge passage,
wherein the first pump, the first gas passage and the water supply passage to a water supply port formed at one end portion at the cultivating chamber side of the water supply passage cooperate to suck decontamination gas from the water discharge port into the first passage and discharge the decontamination gas from the water supply port into the cultivating chamber, and
wherein the passage decontaminating unit drives the first pump to suck the decontamination gas, supplied to the cultivating chamber by the indoor decontaminating unit, from the water discharge port into the first passage and to discharge the decontamination gas from the water supply port into the cultivating chamber, thereby decontaminating the inside of the first passage.

4. The incubator according to claim 1, further comprising:
a second gas passage connected to the upstream side of the filter in the water supply passage at one end thereof, and to a gas discharge portion for discharging gas to the outside at the other end thereof, and
a second pump provided on the second gas passage to suck decontamination gas from a water supply port formed at an end portion at the cultivating chamber of the water supply passage,
wherein the second pump discharges the decontamination gas through the water supply passage and the second gas passage into the gas discharge portion, and
wherein the passage decontaminating unit drives the second pump to suck the decontamination gas, supplied to the cultivating chamber by the indoor decontaminating unit, from the water supply port and to discharge the decontamination gas through the water supply passage and the second gas passage into the gas discharge portion, thereby decontaminating the water supply passage.

5. An incubator, comprising:
a cultivating chamber for cultivating cultures;
a water supply control unit for supplying water into the cultivating chamber through a water supply passage and adjusting the humidity of the inside of the cultivating chamber; and
a filter provided in the water supply passage,
a decontamination liquid tank for stocking decontamination liquid;
a decontamination liquid supply passage connected to an upstream side of the filter in the water supply passage at one end thereof, and to the decontamination liquid tank at the other end thereof; and
a third pump provided on the decontamination liquid passage to make the decontamination liquid flow from the decontamination liquid tank through the decontamination liquid supply passage and the water supply passage to a water supply port formed at an end portion at the cultivating chamber side of the water supply passage,
wherein the passage decontaminating unit that drives the third pump to make the decontamination liquid flow from the decontamination liquid tank through the decontamination liquid supply passage and the water supply passage to the water supply port, thereby decontaminating the water supply passage.

6. An incubator, comprising:
a cultivating chamber including a water supply port for supplying water and a decontamination gas supply port for supplying decontamination gas into the cultivating chamber from a decontaminating unit;
a water stock unit provided in the cultivating chamber, and configured to stock the water to adjust the humidity of the inside of the cultivating chamber;
a water supply tank supplying the water into the water stock unit;
a water supply unit provided between the water stock unit and the water supply tank, said water supply unit including a first passage connected to the water supply port and the water supply tank, the first passage including a filter; and
a passage decontaminating unit including a second passage connected to an upstream side of the filter in the first passage at a first end thereof, said passage decontaminating unit configured such that the decontaminating gas can flow into a part of the first passage, the filter and the second passage.

7. The incubator according to claim 6, further comprising:
a third passage discharging the water stocked in the water stock unit through a water discharge port provided on the water stock unit;
wherein the second passage is connected to the third passage at a second end thereof, and
wherein the passage decontaminating unit is configured such that the decontaminating gas supplied to the cultivating chamber can flow into a part of the third passage.

8. The incubator according to claim 7,
wherein the passage decontaminating unit includes a pump provided on a part of the first passage, a part of the second passage or the part of the third passage, and
wherein the pump is configured to suck the decontamination gas from the water discharge port and to discharge the decontamination gas from the water supply port.

9. The incubator according to claim 6,
wherein the passage decontaminating unit includes a pump provided on the second gas passage,
wherein the second passage is connected to a gas discharge portion for discharging gas to the outside at a second end thereof, and
wherein the pump is configured suck the decontamination gas from the water supply port and discharge the decontamination gas from the gas discharge portion.

10. An incubator, comprising:
a cultivating chamber including a water supply port for supplying water and a decontamination gas supply port for supplying decontamination gas into the cultivating chamber from a decontaminating unit;
a water stock unit provided in the cultivating chamber, and configured to stock the water to adjust the humidity of the inside of the cultivating chamber;
a water supply tank supplying the water into the water stock unit;
a water supply unit provided between the water stock unit and the water supply tank, said water supply unit including a first passage connected to the water supply port and the water supply tank, the first passage including a filter; and
a passage decontaminating unit including a decontamination liquid tank configured to stock decontamination liquid, a second passage connected to an upstream side of the filter in the first passage at a first end thereof, and to the decontamination liquid tank at a second end thereof, said passage decontaminating unit configured such that the decontamination liquid can flow into a part of the first passage, the filter and the second passage.

* * * * *